United States Patent
Yodfat et al.

(10) Patent No.: US 9,387,033 B2
(45) Date of Patent: Jul. 12, 2016

(54) DEVICE AND METHOD FOR ENHANCED SUBCUTANEOUS INSULIN ABSORPTION

(75) Inventors: Ofer Yodfat, Modi'in (IL); Gali Shapira, Haifa (IL); Illai Gescheit, Tel Aviv (IL)

(73) Assignee: Roche Diabetes Care, Inc., Indianapolis, IN (US)

( * ) Notice: Subject to any disclaimer, the term of this patent is extended or adjusted under 35 U.S.C. 154(b) by 416 days.

(21) Appl. No.: 13/060,799

(22) PCT Filed: Aug. 27, 2009

(86) PCT No.: PCT/IL2009/000827
§ 371 (c)(1),
(2), (4) Date: Feb. 25, 2011

(87) PCT Pub. No.: WO2010/023666
PCT Pub. Date: Mar. 4, 2010

(65) Prior Publication Data
US 2011/0160697 A1    Jun. 30, 2011

Related U.S. Application Data

(60) Provisional application No. 61/092,412, filed on Aug. 28, 2008.

(51) Int. Cl.
*A61M 5/14* (2006.01)
*A61M 5/172* (2006.01)
(Continued)

(52) U.S. Cl.
CPC ............ *A61B 18/14* (2013.01); *A61M 5/1413* (2013.01); *A61M 5/14248* (2013.01);
(Continued)

(58) Field of Classification Search
CPC ............ A61M 5/14248; A61M 5/142; A61M 39/0208; A61M 2039/0214; A61M 5/14276; A61M 31/002
USPC ................ 604/20–21, 113–11, 118, 890.144, 604/890.1, 44, 41, 49–50, 181, 131, 134, 604/185, 65–66
See application file for complete search history.

(56) References Cited

U.S. PATENT DOCUMENTS 3,631,847 A    1/1972    Hobbs
3,771,694 A    11/1973    Kaminski
(Continued)

FOREIGN PATENT DOCUMENTS

WO    96/10426    4/1996
WO    2008/106117 A1    9/2008
WO    2008/114218 A2    9/2008

OTHER PUBLICATIONS

International Search Report, Application PCT/IL2009/000827, 2 pages, Dec. 23, 2009.
(Continued)

*Primary Examiner* — Kami A Bosworth
*Assistant Examiner* — Matthew A Engel
(74) *Attorney, Agent, or Firm* — Dinsmore & Shohl LLP

(57) ABSTRACT

Products and methods directed to the improved infusion of fluids are disclosed. Such products and methods can be used to more efficiently and efficaciously administer therapeutic pharmaceuticals to a subject in need of treatment. In many instances, the systems comprise a therapeutic fluid delivery system and a mechanism for enhancing the absorption of the therapeutic fluid. The enhancement of the absorption of the therapeutic fluid is generally performed locally i.e., at or near the site of administration of the therapeutic fluid. The system and methods can be used to deliver any number of therapeutic fluids including but not limited to insulin.

11 Claims, 33 Drawing Sheets

(51) Int. Cl.
*A61B 18/14* (2006.01)
*A61M 5/142* (2006.01)
*A61B 18/20* (2006.01)
*A61B 17/00* (2006.01)
*A61M 5/158* (2006.01)
*A61M 37/00* (2006.01)

(52) U.S. Cl.
CPC ............. *A61M 5/1723* (2013.01); *A61B 18/20* (2013.01); *A61B 2017/00765* (2013.01); *A61M 2005/14268* (2013.01); *A61M 2005/1587* (2013.01); *A61M 2037/0007* (2013.01); *A61M 2205/36* (2013.01); *A61M 2205/3653* (2013.01); *A61M 2230/201* (2013.01)

(56) References Cited

U.S. PATENT DOCUMENTS

| | | | |
|---|---|---|---|
| 4,498,843 A | 2/1985 | Schneider et al. | |
| 4,544,369 A | 10/1985 | Skakoon et al. | |
| 4,657,486 A | 4/1987 | Stempfle et al. | |
| 4,698,062 A | 10/1987 | Gale et al. | |
| 4,709,698 A * | 12/1987 | Johnston et al. | 606/41 |
| 4,715,786 A | 12/1987 | Wolff et al. | |
| 5,616,127 A * | 4/1997 | Smith | 604/118 |
| 5,658,278 A * | 8/1997 | Imran et al. | 606/41 |
| 5,957,895 A * | 9/1999 | Sage et al. | 604/181 |
| 6,306,431 B1 | 10/2001 | Zhang et al. | 424/449 |
| 6,485,461 B1 * | 11/2002 | Mason et al. | 604/132 |
| 6,508,785 B1 * | 1/2003 | Eppstein | 604/113 |
| 6,530,915 B1 * | 3/2003 | Eppstein et al. | 606/2 |
| 6,558,351 B1 | 5/2003 | Steil et al. | |
| 6,589,229 B1 * | 7/2003 | Connelly et al. | 604/890.1 |
| 6,685,699 B1 * | 2/2004 | Eppstein et al. | 606/2 |
| 6,723,072 B2 | 4/2004 | Flaherty et al. | |
| 6,740,059 B2 | 5/2004 | Flaherty | |
| 6,749,587 B2 * | 6/2004 | Flaherty | 604/151 |
| 6,756,053 B2 * | 6/2004 | Zhang et al. | 424/449 |
| 7,104,767 B2 * | 9/2006 | Lee | 417/413.1 |
| 7,429,258 B2 * | 9/2008 | Angel | A61M 5/155 604/140 |
| 7,591,801 B2 * | 9/2009 | Brauker et al. | 604/161 |
| 7,682,338 B2 * | 3/2010 | Griffin | 604/164.07 |
| 7,885,697 B2 * | 2/2011 | Brister et al. | 600/347 |
| 7,955,297 B2 * | 6/2011 | Radmer et al. | 604/93.01 |
| 8,147,446 B2 * | 4/2012 | Yodfat et al. | 604/67 |
| 8,231,532 B2 * | 7/2012 | Say et al. | 600/365 |
| 8,244,377 B1 * | 8/2012 | Pianca et al. | 607/126 |
| 8,486,278 B2 * | 7/2013 | Pang | A61F 9/00781 216/2 |
| 8,741,336 B2 * | 6/2014 | DiPierro | A61K 31/135 424/449 |
| 2003/0138464 A1 * | 7/2003 | Zhang et al. | 424/400 |
| 2004/0220456 A1 | 11/2004 | Eppstein | |
| 2004/0220551 A1 * | 11/2004 | Flaherty et al. | 604/890.1 |
| 2006/0135911 A1 | 6/2006 | Mittur | |
| 2007/0066939 A1 * | 3/2007 | Krulevitch et al. | 604/152 |
| 2007/0219480 A1 * | 9/2007 | Kamen | G01F 22/00 604/20 |
| 2008/0077081 A1 * | 3/2008 | Mounce et al. | 604/67 |
| 2008/0215035 A1 * | 9/2008 | Yodfat et al. | 604/513 |
| 2008/0281297 A1 * | 11/2008 | Pesach et al. | 604/890.1 |
| 2009/0163855 A1 * | 6/2009 | Shin et al. | 604/66 |
| 2009/0311133 A1 * | 12/2009 | Pang | A61F 9/00781 422/22 |
| 2011/0160697 A1 * | 6/2011 | Yodfat | A61B 18/14 604/506 |
| 2011/0264028 A1 * | 10/2011 | Ramdas et al. | 604/20 |
| 2011/0313357 A1 * | 12/2011 | Skutnik | A61M 5/14248 604/151 |
| 2012/0029333 A1 * | 2/2012 | Dogwiler | A61M 5/158 600/365 |
| 2012/0302942 A1 * | 11/2012 | DiPierro | A61K 31/135 604/23 |
| 2014/0058353 A1 * | 2/2014 | Politis et al. | 604/506 |

OTHER PUBLICATIONS

Koivisto, Sauna-induced acceleration in insulin absorption from subcutaneous injection site, Br Med J., 280(6229): 1411-1413, 1980.
Durand, et al., Vasodilatation in response to repeated anodal current application in the human skin relies on aspirin-sensitive mechanisms, Journal of Physiology, 540(1): 261-269, 2002.
Tartas, et al., Early vasodilator response to anodal current application in human is not impaired by cyclooxygenase-2 blockade, Am J Physiol Heart Circ Physiol, 288(4): 1668-1673, 2005.
Ramsay, et al., Vascular changes in human skin after ultraviolet irradiation, British Journal of Dermatology, 94(5), pp. 487-493, 1976, Abstract.

* cited by examiner

DEVICE AND METHOD FOR ENHANCED SUBCUTANEOUS INSULIN ABSORPTION

CROSS-REFERENCE TO RELATED APPLICATIONS

This application is the U.S. national stage entry under 35 USC §371 of International Application No. PCT/IL2009/000827, filed Aug. 27, 2009, which claims priority to U.S. provisional application Ser. No. 1/092,412entitled "Device and Method for Enhanced Subcutaneous Insulin Absorption", filed Aug. 28, 2008, the content of which is hereby incorporated by reference in its entirety.

FIELD

The present invention relates generally to a method and a device for sustained infusion of fluids. More particularly, the invention relates to a skin securable device that delivers fluid to the subcutaneous tissue and a method for enhancement of fluid absorption into the systemic circulation.

BACKGROUND

Diabetes Mellitus and Insulin Pumps

Diabetes mellitus is a disease of major global importance, increasing in frequency at almost epidemic rates, such that the worldwide prevalence in 2006 is 170 million people and predicted to at least double over the next 10-15 years. Diabetes is characterized by a chronically raised blood glucose concentration (hyperglycemia), due to a relative or absolute lack of the pancreatic hormone, insulin.

Treatment of diabetes mellitus requires frequent insulin administration that can be done by multiple daily injections (MDI) with syringe or by continuous subcutaneous insulin injection (CSII) with insulin pumps. In recent years, ambulatory portable insulin infusion pumps have emerged as a superior alternative to multiple daily injections of insulin. These pumps, which deliver insulin to the subcutaneous tissue at a continuous basal rate as well as in bolus volumes, were developed to liberate patients from repeated self-administered injections, and allow greater flexibility in dose administration.

Several ambulatory insulin infusion devices are currently available on the market. Examples of first generation disposable syringe-type reservoir and tubes were disclosed in U.S. Pat. No. 3,631,847 to Hobbs, U.S. Pat. No. 3,771,694 to Kaminski, U.S. Pat. No. 4,657,486 to Stempfle, and U.S. Pat. No. 4,544,369 to Skakoon. Other dispensing mechanisms have also been disclosed, including peristaltic positive displacement pumps, in U.S. Pat. No. 4,498,843 to Schneider and U.S. Pat. No. 4,715,786 to Wolff.

Although these devices represent an improvement over multiple daily injections, they nevertheless all suffer from several drawbacks. The main drawback is the large size and weight of the device, caused by the configuration and the relatively large size of the driving mechanism and of the syringe. This relatively bulky device has to be carried in a patient's pocket or attached to the belt. Consequently, the fluid delivery tube of the infusion set is very long, usually longer than 60 cm, in order to permit needle insertion at remote sites of the body. These uncomfortable bulky devices and long infusion set are rejected by the majority of diabetic insulin users, since they disturb regular activities, such as sleeping and swimming. In addition, the delivery tube excludes some optional remote insertion sites, like buttocks, arms and legs.

To avoid the consequences of a long infusion set, a new concept, a second generation pump, has been proposed. This concept includes a remote controlled skin adherable device with a housing having a bottom surface adapted to contact patient's skin, a reservoir disposed within the housing, and an injection needle adapted to communicate with the reservoir. These skin adherable devices are disposed every 2-3 days similarly to available pump infusion sets. These devices were disclosed at least in U.S. Pat. No. 5,957,895 to Sage, U.S. Pat. No. 6,589,229 to Connelly, and U.S. Pat. No. 6,740,059 to Flaherty. Additional configurations of skin adherable pumps were disclosed in U.S. Pat. No. 6,723,072 to Flaherty and U.S. Pat. No. 6,485,461 to Mason. These devices also have several limitations: they are also bulky and expensive. Their high selling price is due to the high production and accessory costs; the user must discard the entire device every 2-3 days, including the relatively expensive components, such as the driving mechanism and electronics.

A third generation dispensing device, described in co-pending/co-owned U.S. patent application Ser. No. 11/397,115, and International Patent Application Nos. PCT/IL06/001276 and PCT/IL09/000,388, whose disclosures are hereby incorporated by reference in their entireties, has been recently developed. This third-generation device is a miniature portable programmable fluid dispenser that has no tubing and can be attached to the patient skin. It is composed of two parts, a disposable part (DP) and a reusable part (RP). After connection of the reusable and the disposable parts, the unified dispensing unit presents a thin profile. The RP contains electronics and other relatively expensive components and the DP contains reservoir. This device comprises a remote control unit that allows data acquisition, programming, and user inputs. An improvement to the skin adherable pump disclosed above is described in co-pending/co-owned U.S. patent application Ser. No. 12/004,837 and International Patent Application No. PCT/IL07/001,578, the disclosures of which are also incorporated herein by reference in their entireties. In this application, an improved system and a method for connection and disconnection of a skin securable pump is disclosed. The method uses a cradle, which is initially adhered to the skin and then a cannula is inserted through the cradle into the body of the user. The two-part pump can be consequently connected and disconnected to and from the cradle upon patient's discretion.

Partly in response to the need for tighter glycemic control, closed loop infusion systems, as the system described in U.S. Pat. No. 6,558,351 assigned to Medtronic MiniMed, have been developed. This system comprises a sensor system (e.g. a continuous glucose monitor, CGM), and a delivery system (i.e., insulin pump). The systems are interconnected via a controller a separate components, both comprising separate tubing and separate cannulae that are applied to the body of the user. A new generation of a dual function device and/or system is described in U.S. patent application Ser. Nos. 11/706,606 and 11/963,481, and in International Patent Application No. PCT/IL08/001,521, whose disclosure is also incorporated by reference in its entirety, assigned to Medingo Ltd. The device is a single skin securable patch employing a single subcutaneous cannula.

One of the main hurdles in perfecting a semi-invasive closed loop system (i.e., sensor and delivery systems located in the subcutaneous tissue) stems from the lag time between insulin delivery and peak glucose lowering effect. This lag time can be shortened with development of more rapid insulin analogues and/or with better insulin absorption from the subcutaneous tissue.

Insulin Absorption

When a bolus of rapid acting insulin, commonly used in insulin pumps, is administered to the subcutaneous tissue before a meal, insulin effect usually lags behind glucose absorption and consequently blood glucose rises and peaks, as can be seen in FIG. 1. This figure shows curves of blood glucose and insulin levels (y axis) over time (x axis) after a meal intake and an insulin bolus, and the lag period between glucose and insulin blood levels peaks. Blood insulin levels usually lag behind blood glucose levels when insulin is administered at the time of oral glucose intake. This phenomenon consequently leads to blood glucose rises and peaks, as can be seen in the figure. An enhanced absorption of insulin will shorten the lag period between glucose and insulin blood levels' peaks and thus mitigate the described postprandial hyperglycemia.

Changes in blood glucose concentrations are proportional to rate of insulin absorption from the injection site into the systemic circulation. This absorption rate is determined by several factors, including the circulation of blood in the vicinity of the injection site, and the permeability of the walls of the relevant blood vessels. Insulin absorption at the injection site is enhanced with increased blood flow and/or blood vessel wall permeability at the subcutaneous tissue and reduced with decreased blood flow and/or blood vessel wall permeability. Increased subcutaneous blood flow and/or blood vessel wall permeability may be promoted by vasodilatation of the subcutaneously located blood vessels. Such vasodilatation may be achieved by different methods, including the following:

Local heat; It has been shown that, for example, the disappearance rate of insulin from subcutaneous tissue in the sauna was two-fold greater than in room temperature (Br Med J. 1980 Jun. 14; 280(6229): 1411-1413). U.S. Pat. No. 6,756,053 assigned to Zars Inc., describes a method for enhanced transdermal drug delivery by controlled heating. One method for providing controlled heating is ultra sound; Ultra Sound is commonly used to generate deep heat in physical therapy and as an adjunct to wound healing by promoting blood flow to the injured tissue. Another method for achieving local heating is high frequency vibration.

Current application; Monopolar current applications are often used to increase the migration of vasoactive drugs through the skin, a technique known as iontophoresis. It has been reported that in parallel to the 'specific' vasomotor physiological effect resulting from the diffused drug, a 'non-specific' vasodilatation occurs as a result of the current application itself. The amplitude of this current-induced vasodilatation depends on the electrical charge (Journal of Physiology 2002, 540(1), 261-269). The 'non-specific' vasodilatory effect can be applied intentionally to achieve enhanced subcutaneous blood flow.

UV light; Increased blood flow after low dose irradiation of the human skin with UV at 250 and 300 mu has been demonstrated (British Journal of Dermatology 1976 94 (5) 487-493).

Pharmacologic agents; Agents such as nitroglycerin, nitroprusside, histamine, PDE5 inhibitors (e.g., sildenafil), and papaverine are vasodilating agents known in the art.

In order to achieve an accelerated insulin absorption rate and thus a more rapid glucose lowering effect, it is desirable to provide an insulin pump and a method for accelerating insulin absorption by promoting a vasodilatory effect on the subcutaneous blood vessels.

It is also desirable to provide a device that delivers insulin into the body and can concomitantly monitor body glucose (e.g., blood, ISF) levels and a method for promoting a vasodilatory effect on the subcutaneously located blood vessels. More specifically, it is advantageous to provide an improved semi-invasive closed loop drug delivery system (i.e., sensor and delivery systems located in the subcutaneous tissue) wherein the lag time between delivery of the drug (e.g., insulin) and peak pharmaceutical effect (e.g., glucose lowering), which comprises a mechanism for increasing drug absorption from the subcutaneous tissue.

It is also desirable to provide a device which is miniature, discreet, economical for the users and highly cost effective and a method for promoting a vasodilatory effect on the subcutaneous blood vessels.

It is also desirable to provide a device that contains a miniature skin securable dispensing patch unit that can continuously dispense insulin and a method for promoting a vasodilatory effect on the subcutaneous blood vessels.

It is also desirable to provide a device that comprises an insulin dispensing patch unit that can be remotely controlled and a method for promoting a vasodilatory effect on the subcutaneous blood vessels.

It is also desirable to provide a device that contains a miniature skin securable patch that can continuously dispense insulin and monitor body glucose concentration levels and a method for promoting a vasodilatory effect on the subcutaneous blood vessels.

It is also desirable to provide a miniature skin securable patch that can continuously dispense insulin and continuously monitor body glucose concentration levels and a method for promoting a vasodilatory effect on the subcutaneous blood vessels.

It is also desirable to provide a device that includes a closed or semi-closed loop system that is capable of monitoring glucose levels and dispensing insulin according to the sensed glucose levels and a method for promoting a vasodilatory effect on the subcutaneous blood vessels.

SUMMARY

The present invention discloses a portable device that delivers therapeutic fluid into the body (i.e., insulin) and a method for enhancing therapeutic fluid absorption from the injection site into the systemic circulation.

The dispensing device according to the invention comprises a dispensing patch unit and in some preferred embodiments a remote control unit which communicates with the dispensing patch unit and allows programming of therapeutic fluid delivery, user input and data acquisition. The dispensing patch unit can be connected to a subcutaneously cannula through which insulin is delivered to the body. In some preferred embodiment, the patch unit is composed of two parts—a disposable part (DP) and a reusable part (RP). In one preferred embodiment a cradle unit is provided which is a flat sheet that adheres to the skin and allows patch disconnection and reconnection upon patient discretion. After attachment of the cradle unit to the skin, a cannula is inserted into the subcutaneous compartment through a dedicated passageway in the cradle unit.

In one aspect, the invention contemplates an improved semi-invasive closed loop drug delivery system (i.e. sensor and delivery systems located in the subcutaneous tissue) wherein the lag time between delivery of the drug (e.g. insulin) and peak pharmaceutical effect (e.g., glucose lowering), which comprises a mechanism for increasing drug absorption from the subcutaneous tissue. In one embodiment the increase in drug absorption is accomplished through, vasodilatation. In a preferred embodiment the vasodilatation is accomplished through heating of the tissue at the site of drug delivery. In a most preferred embodiment both the heating and drug delivery are subcutaneous.

In one preferred embodiment the dispensing device comprises means for enhancing therapeutic fluid absorption into the systemic circulation by prompting vasodilatation of subcutaneous blood vessels.

In another aspect, the invention contemplates a system and/or a device for delivering therapeutic fluid to a body of a patient comprising a dispensing unit including a reservoir for retaining the therapeutic fluid, a driving mechanism to dispense the therapeutic fluid from the reservoir to the body of the patient, a controller to control, at least in part, operation of the driving mechanism, a power source to power at least the driving mechanism and the controller; and an absorption enhancement device for increasing the absorption rate of the therapeutic fluid in the body of the patient.

In one embodiment of the invention, the system further comprises a first subcutaneously insertable element for delivering the therapeutic therethrough to the body of the patient. In a preferred embodiment, the subcutaneously insertable element is a cannula. In a more preferred embodiment, the absorption enhancement device comprises at least one electrode disposed on the cannula, the electrode being capable of heating the local surrounding tissue i.e., the tissue surrounding the at least one electrode.

In another embodiment of the invention, the system comprises a first and a second subcutaneously insertable element. The first subcutaneously insertable element used to deliver the therapeutic therethrough to the body of the patient. The second subcutaneously insertable element having at least one electrode disposed thereon capable of heating local surrounding tissue.

Wherein the invention contemplates the use of one or more electrodes, the electrodes would generally be electrically connected to a power source, and the controller would control the driving mechanism to deliver the therapeutic fluid to the body and the at least one electrode to heat the local surrounding tissue, although separate controllers could be used to control the therapeutic fluid delivery and the at least one electrode.

In a further aspect of the invention, the system may comprise a dispensing unit including at least one housing, wherein the absorption enhancement device comprises one or more heating plates disposed on the at least one housing to heat the patient's skin surface.

In some embodiments, the system further comprises a skin adherable cradle unit that contains the absorption enhancement device and wherein the absorption enhancement device includes one or more heating plates to heat the patient's skin surface.

In another embodiment of the system of the invention, the absorption enhancement device further comprises a first and a second subcutaneously insertable element. The first subcutaneously insertable element is being used to deliver the therapeutic fluid therethrough to the body of the patient. The second subcutaneously insertable element is being used to deliver a chemical absorption enhancing agent such as a vasodilator (also referred-to as "vasodilatory agent"). In an alternative embodiment, a single subcutaneously insertable element can be used to deliver both the therapeutic fluid and the vasodilatory agent. In a preferred embodiment, the subcutaneously insertable element or elements comprise one or more cannulae, the cannulae having one or more lumens. The vasodilatory agent may be delivered in any number of methods. In one embodiment, the vasodilatory agent is delivered through the use of one or more micro-needles.

The vasodilatory agent may be retained in the dispensing unit of the system of the invention in either the same reservoir as the therapeutic fluid or in a separate second reservoir.

The system of the invention may also comprise a cradle unit having a plurality of wells to receive a plurality of subcutaneously insertable elements. In one embodiment, the cradle unit has a plurality of micro-openings to receive an array of micro-needles.

In another aspect, the absorption enhancement device of the system of the invention comprises a vibration mechanism capable of vibrating in a high frequency causing an increase of therapeutic fluid absorption rate in the body.

In another aspect, the absorption enhancement device of the system of the invention comprises an energy emitting source. The energy emitting source may take many forms including but not limited to a system for emitting UV energy, IR radiation, and/or acoustic waves.

In one embodiment, the systems described above can further include one or more sensors for monitoring tissue properties corresponding with the change in therapeutic fluid absorption rate. The sensor or sensors can take any number of forms including but not limited to a thermometer to measure temperature, a radiation detector, a pressure sensor, an acoustic sensor, and a chemical sensor measuring concentration level of an agent.

In a further embodiment, the controller of the system controls the operation of the absorption enhancement device based on one or more signals received from the sensor.

In another aspect the system of the invention, the system further comprises an analyte sensing device, such as a glucometer or a continuous glucose monitor (CGM), or a device that senses another analyte of interest. In a preferred embodiment, the analyte sensing device sends a signal to the system's controller and the controller controls the absorption enhancement device based on the signal.

The therapeutic agent or drug that the system delivers can be any therapeutic fluid. In a preferred embodiment the therapeutic agent is insulin. The vasodilatory agent also can be any number of compounds including but not limited to one or more of the following, alone or in combination: nitroglycerin, nitroprusside, histamine, PDE5 inhibitors, sildenafil, and papaverine.

In another aspect, the invention contemplates a method of enhancing absorption of a pharmaceutical agent or drug comprising applying an absorption enhancing stimulus to a drug administration site, and administering the drug to a subject in need of the drug. In a preferred embodiment, the absorption enhancing stimulus is applied locally to the drug administration site. Although various drugs and absorption enhancing agents are contemplated, in a preferred embodiment the drug is insulin.

The absorption enhancing agent may be applied prior to, after or at the same time as the administration of the drug. In a preferred embodiment, the absorption enhancing agent is applied prior to administration of the drug.

Although the method of the invention contemplates various modes of drug administration (e.g., transdermal, subcutaneous etc.), in a preferred embodiment, the method of the invention contemplates subcutaneous administration of the drug.

The absorption enhancing agent may take many forms including the direct application of heat using thermal electrodes, the application of ultrasonic energy, high frequency vibration, the application of electrical current, and/or chemical means such as a chemical vasodilator. Additionally, the absorption enhancing agent may be applied at various locations local to the drug administration site (e.g., transdermally, subcutaneously etc.). In a preferred embodiment, the absorption enhancing agent is heat (i.e., thermal energy). In a more preferred embodiment, the heat is applied subcutaneously.

According to one embodiment of the present invention, vasodilatation of subcutaneous blood vessels can be achieved by local heating of the injection site. The heating element (i.e., thermal electrodes, high frequency vibrator, etc.) can reside subcutaneously disposed on the cannula, on additional designated heating probe, or above the skin connected to the dispensing patch unit or cradle unit.

According to another embodiment of the present invention, vasodilatation of subcutaneously located blood vessels can be achieved by electrical current application. The electrical charge (i.e., current*time, $Q=I*t$, for example—2-15 mC) can be applied transcutaneously or subcutaneously by virtue of electrodes disposed on the surface of the subcutaneously insertable cannula. Alternatively, electrodes can be disposed on a subcutaneously located probe dedicated solely for providing current induced vasodilatation. According to one embodiment, a segmented current application is applied which has better vasodilatation effect than "at once" charge delivery. (Journal of Physiology 2002, 540(1), 261-269). The vascular response to galvanic current application is suggested to rely on an axon reflex and neurogenic inflammation with either anodal or cathodal current. The axon reflex-related cutaneous vasodilatation relies on the local release of neural primary afferent fibers mediators such as calcitonin gene-related peptide, substance P, and prostaglandin (Am J Physiol Heart Circ Physiol 2005, 288:668-673).

According to another embodiment of the present invention, vasodilatation of subcutaneous blood vessels can be achieved by application of laser that emits radiation in the UV spectrum range. Application of the UV laser beam may be either continuous or pulsed. Use of a pulsed laser reduces heat built-up and subsequent damage to the tissue. According to one such embodiment, the UV radiation wavelength is in the range of 150-400 nm.

According to another embodiment of the present invention, vasodilatation of subcutaneously located blood vessels can be achieved by concomitant administration of vasodilating pharmacologic agents (e.g., nitroglycerin, nitroprusside, histamine, PDE5 inhibitors). Alternatively the vasodilating pharmacologic agent is delivered prior to, or immediately after, the administration of the therapeutic fluid (e.g., insulin). Administration of the vasodilating pharmacologic agent can be done via the same cannula used for delivery of the therapeutic fluid (e.g., insulin) or via a dedicated cannula/probe. Alternatively, delivery of the vasodilating pharmacologic agent can be done by virtue of an may of microneedles that merely penetrate the stratum corneum layer of the skin.

According to one embodiment, administration of the vasodilating pharmacologic agent can be provided transdermally (i.e., topical application or transdermal patch).

According to one embodiment of the present invention, vasodilatation of subcutaneously located blood vessels can be achieved by a combination of any of the methods described in the abovementioned embodiments.

According to one embodiment of the present invention, enhancement of therapeutic fluid (e.g. insulin) absorption is performed only when bolus dosages are administered. According to one such embodiment, enhancement of therapeutic fluid (e.g. insulin) absorption is performed only when bolus dosages greater than a certain threshold value are administered.

The invention further contemplates a method of administering a therapeutic fluid to a body of a patient comprising providing (a) a dispensing device including a reservoir retaining the therapeutic fluid, a driving mechanism to dispense the therapeutic fluid from the reservoir to the body of the patient; and (b) an absorption enhancement device which causes an increase in the absorption rate of the therapeutic fluid in the body of the patient. The absorption enhancement device is initiated and the therapeutic fluid or drug is administered to the body of the patient.

In one embodiment, the method of administering the therapeutic fluid comprises inserting a cannula into the body of the patient, the cannula including the absorption enhancement device. The therapeutic fluid is preferably delivered through the cannula.

In another aspect of the invention, the method of administration contemplates that the absorption enhancement device includes a heater, and wherein the method comprises the initiation of the absorption enhancement device includes controlling the heater to locally elevate the temperature in surrounding tissue. In a preferred embodiment, at least part of the absorption enhancement device is located subcutaneously. In a more preferred embodiment, the therapeutic fluid administration and temperature elevation occur substantially in the same insertion site.

In another aspect of the invention, the method of administration comprises the administration of a vasodilatory agent to the body of the patient.

In yet another aspect of the invention, the method of administration includes inserting a first subcutaneously insertable element into the body of the patient to deliver the therapeutic fluid therethrough, and inserting a second subcutaneously insertable element having the absorption enhancement device.

In another aspect of the invention, the method of administration may include the further step of monitoring a change corresponding to the therapeutic fluid absorption rate, which may or may not be used to control (directly or indirectly) either therapeutic fluid delivery and/or therapeutic fluid absorption enhancement.

DETAILED DESCRIPTION

Figure 1:
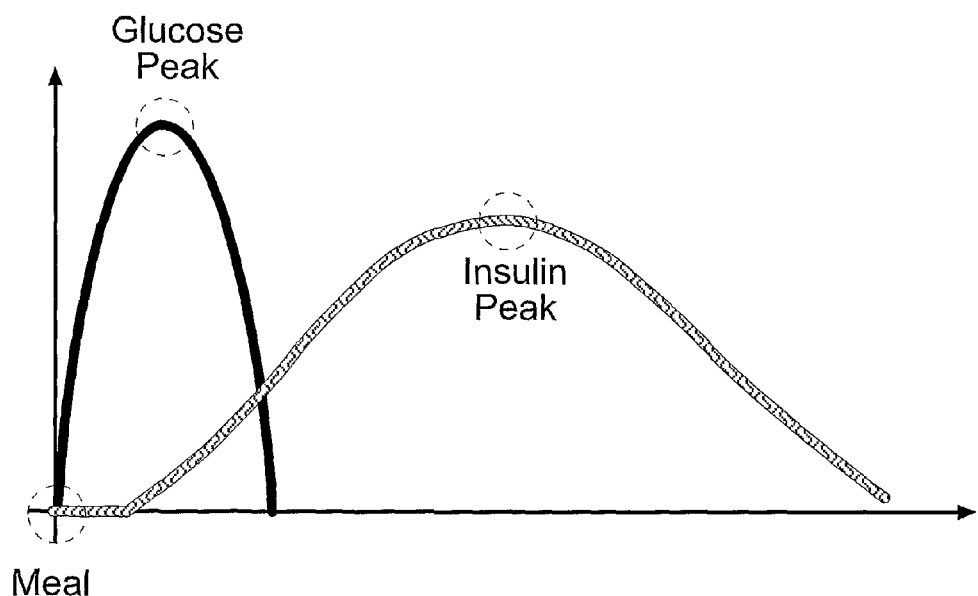
FIG. 1 shows curves of blood glucose and insulin levels over time after a meal intake and an insulin bolus, and the lag period between glucose and insulin blood levels peaks.
Figure 2:
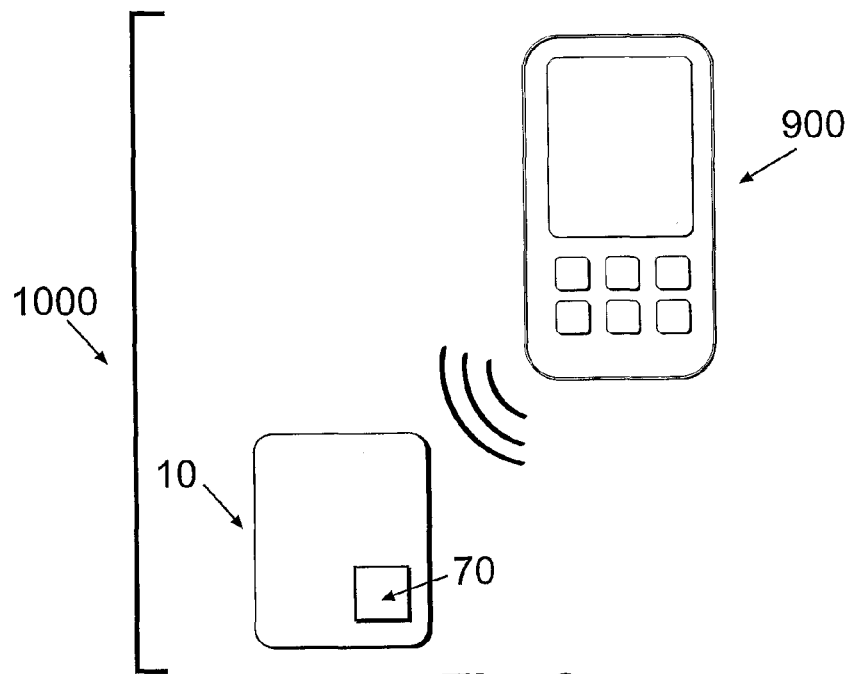
FIG. 2 illustrates an exemplary fluid delivery device according to some embodiments of the present disclosure. The device is composed of dispensing unit and remote control unit.

FIG. 2 illustrates a fluid delivery device 1000 for medical infusion of therapeutic fluid(s) (for example—insulin), into a body of a patient. The device 1000 comprises a dispensing unit 10 and a remote control unit 900. The dispensing unit 10 comprises a means for enhancing subcutaneous absorption of the delivered fluid 70.

Figure 3:
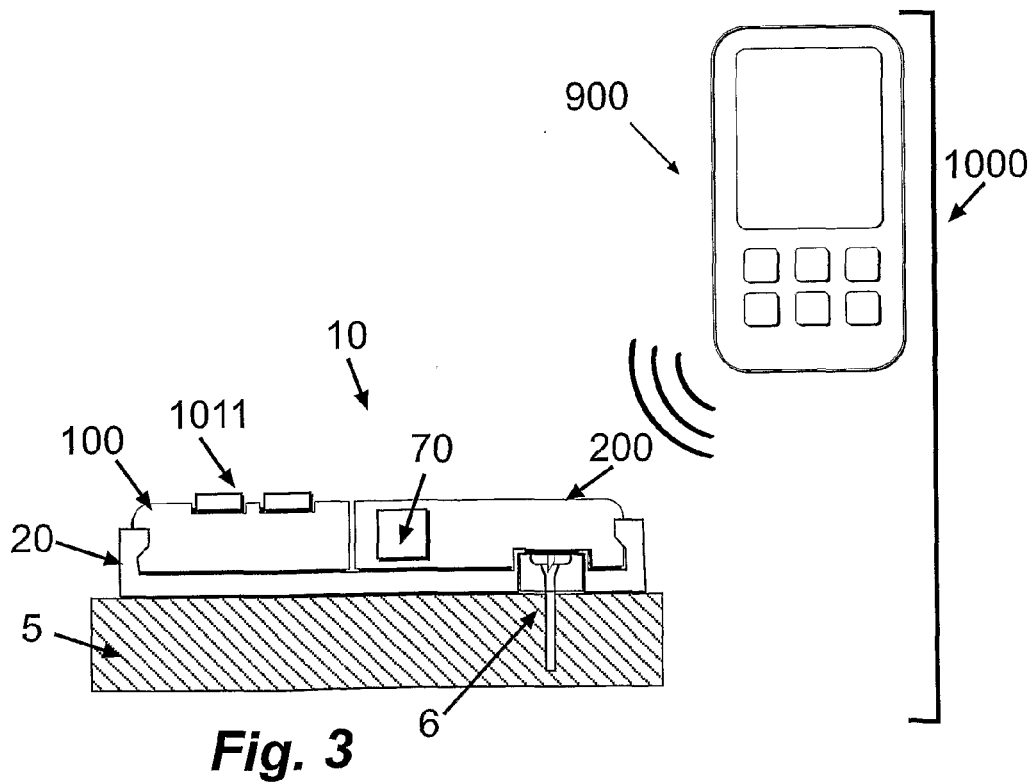
FIG. 3 shows the insulin infusion device comprising a dispensing unit and a remote control unit. The dispensing unit contains a means for enhancing therapeutic fluid absorption according to some embodiments of the invention.

FIG. 3 shows an insulin infusion device 1000 according to some embodiments of the invention comprising a dispensing patch unit 10, which can be secured to the user's skin 5, and a remote control unit 900, which communicates with the dispensing patch unit 10, allowing programming, user inputs and data acquisition.

In one embodiment, the patch unit comprises a driving and pumping mechanism (either separately provided or integral with one another), a reservoir and an exit port. The patch unit may comprise a reservoir, a driving mechanism such as an electrical DC or stepper motor, a shape memory alloy actuator, or the like and/or a pumping mechanism such as a peristaltic pump, a syringe, or the like. The patch unit may also comprise a power supply means and electronic components. The patch unit can be composed of one part or two parts, namely a reusable part and a disposable part and can be connected to and disconnected from the needle unit. In some embodiments, the needle unit comprises a penetrating member with connected thereto cannula, well and cradle.

The patch unit 10 can be connected to a cannula 6 that penetrates the skin 5 to allow delivery of insulin to a patient. The patch unit 10 can be attached to a dedicated cradle unit 20 that is a flat sheet adhered to the user's skin 5 and allows connection/disconnection of the patch unit 10. An exemplary embodiment of this arrangement is discussed in a co-owned, A2co-pending U.S. patent application Ser. No. 12/004,837, the disclosure if which is hereby incorporated by reference in its entirety.

Manual inputs can be carried out by one or more buttons 1011 located on the dispensing patch unit 10. The dispensing patch unit 10 can be composed of one housing or two housings comprising reusable 100 and disposable 200 parts as shown in our previous patent application U.S. Ser. No. 11/397,115 and International Patent Application PCT/IL09/000,388, the disclosures of which are hereby incorporated by reference in their entireties.

In accordance with the invention, a means for enhancing subcutaneous insulin absorption 70 is incorporated within the patch unit 10. The absorption enhancing means 70 can be incorporated in the disposable part 200, reusable part 100, cradle unit 20, cannula 6, or any combination of the above-mentioned parts and/or units.

Figure 4A:
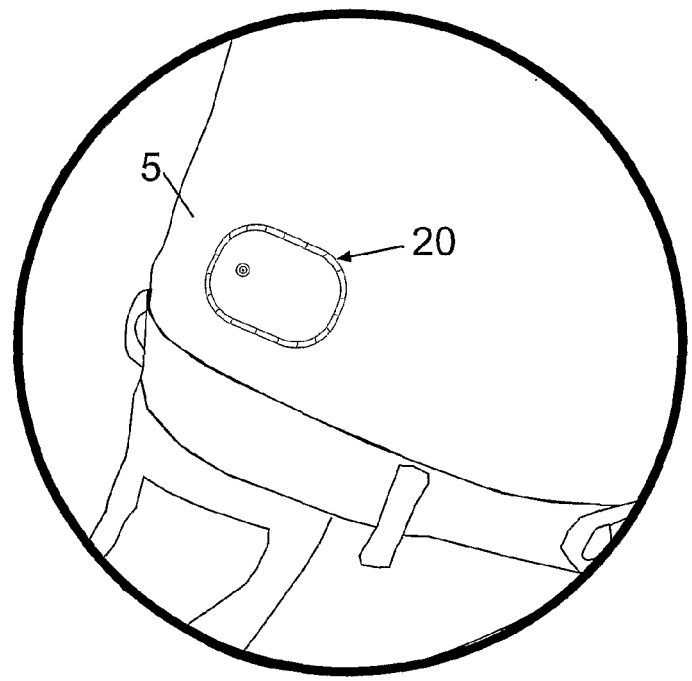
FIGS. 4a-4c illustrate the attachment of the dispensing unit to a skin securable cradle unit.
Figure 4B:
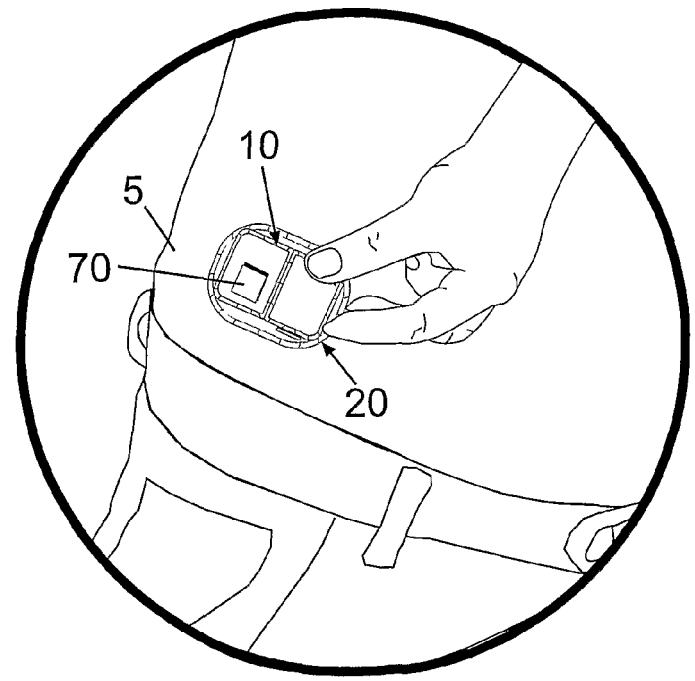
Figure 4C:
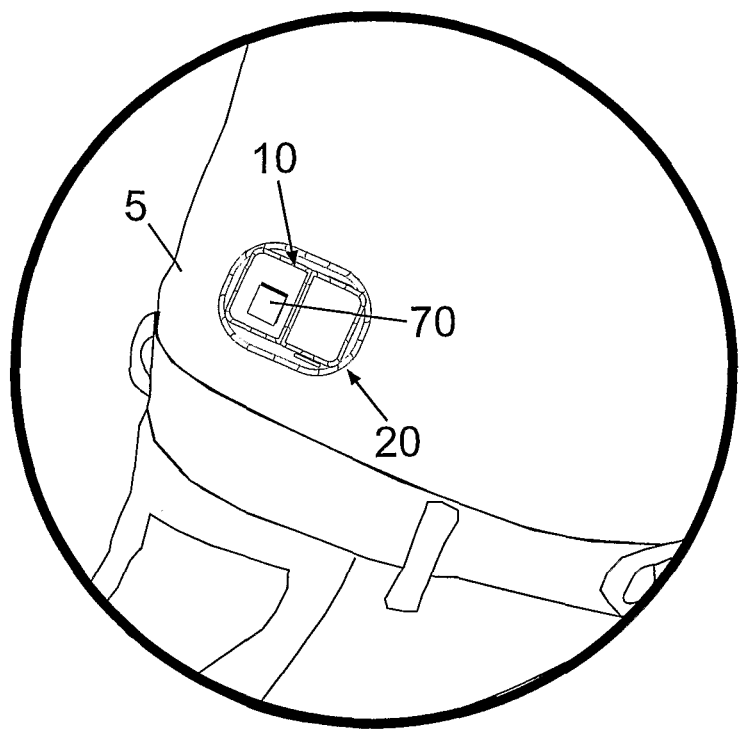

FIGS. 4a-4c illustrate a fluid delivery device that includes a cradle unit 20 that can be adhered to the skin 5 of the user. The dispensing unit 10 can then be connected to and disconnected from the cradle unit 20 upon patient's discretion. FIG. 4a illustrates the cradle unit 20 adhered to the skin 5. FIG. 4b illustrates the connection of the dispensing unit 10 to the cradle unit 20. FIG. 4c illustrates the dispensing unit 10 connected to the cradle unit 20 and ready for operation.

In accordance with the invention, a means for enhancing subcutaneous insulin absorption 70 is incorporated in the dispensing patch unit 10. The absorption enhancing means can alternatively (not shown) be incorporated in the cradle unit 20, the cannula (not shown), or any combination of the abovementioned parts and/or units.

Figure 5:
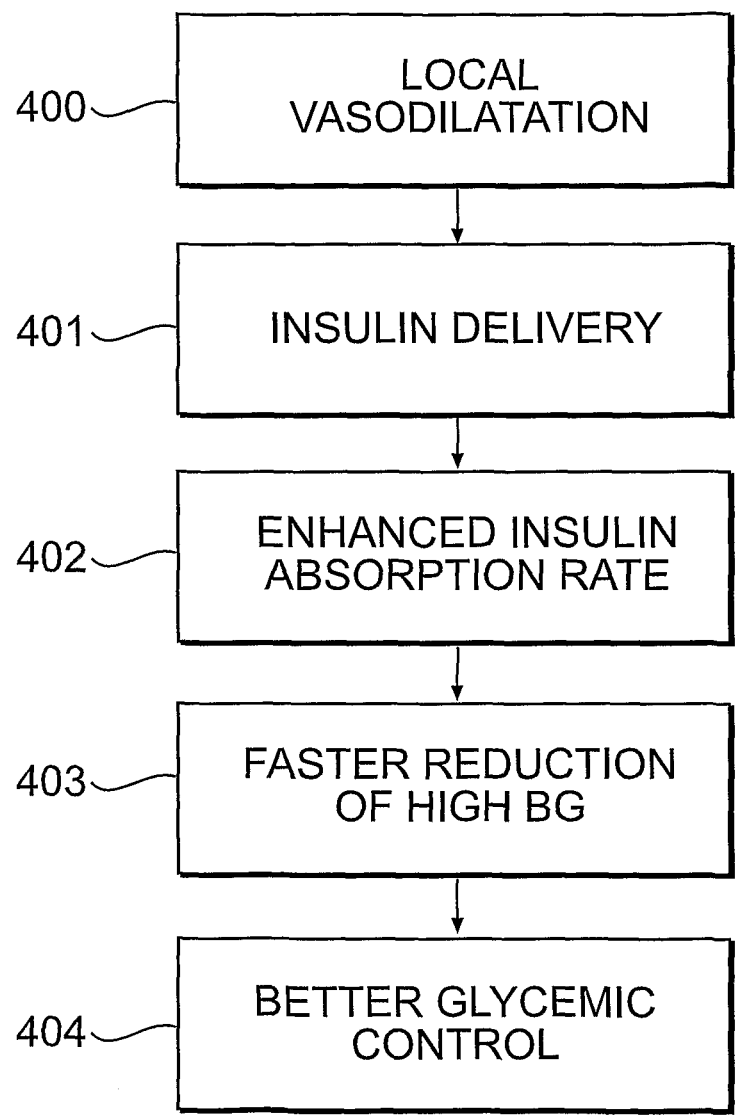
FIG. 5 is a block diagram representing the rationale behind incorporating a vasodilatation means in an insulin infusion device.

FIG. 5 is a block diagram representing the rationale behind incorporating a vasodilatation means in an insulin infusion device. The initial step 400 of local vasodilatation (also referred-to as "vasodilation"), which can be achieved in a variety of methods as detailed in the following figures, is followed by insulin delivery, at step 401, to a locally vasodilated subcutaneous tissue. At step 402, enhanced insulin absorption is obtained, consequently leading to a faster reduction of high blood glucose at step 403, and to better glycemic control immediately and in the long run 404. An optional mechanism for the enhanced insulin'absorption is that the increased blood flow obtained by the vasodilatation in step 400 raises the concentration gradient across the blood vessel and therefore enhances absorption by passive diffusion. Vasodilatation achieved by local heat generation may also cause enhanced absorption by increasing vessel wall permeability and drug solubility.

Figure 6:
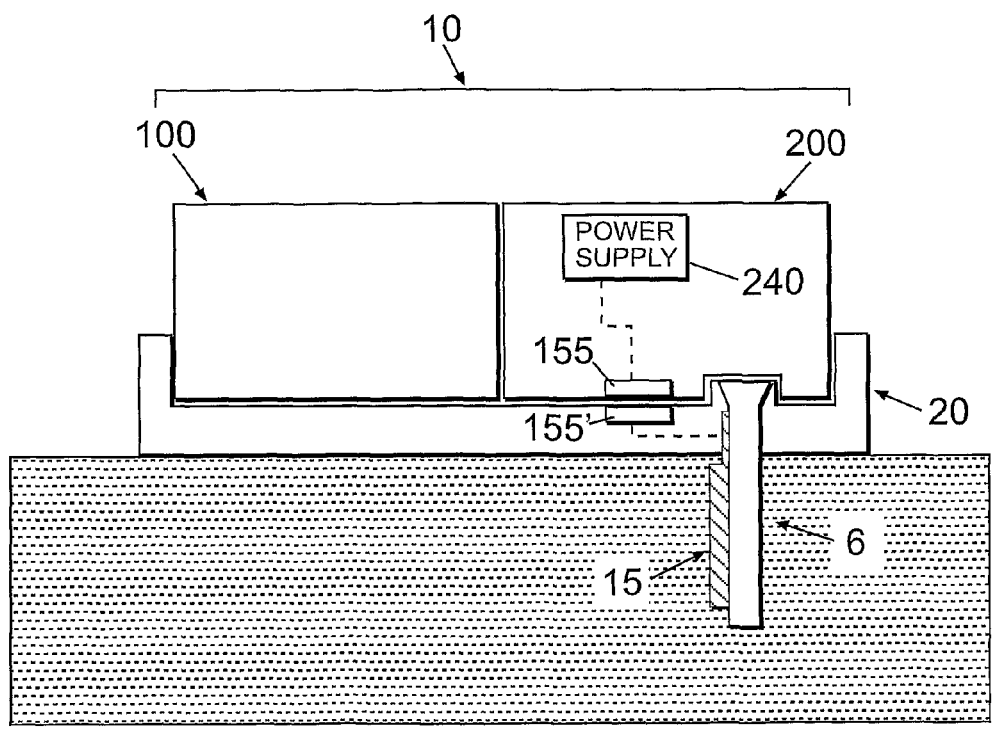
FIG. 6 shows a dispensing patch unit comprising a means for enhancing subcutaneous insulin absorption by local heating of the injection site with electrodes disposed on the surface of the subcutaneously inserted cannula.

FIG. 6 shows a dispensing patch unit 10 comprising a means for enhancing subcutaneous insulin absorption by local heating of the injection site by heating at least one electrode 15 disposed on the surface of the subcutaneously inserted cannula 6 through which insulin is delivered. The heating electrode/electrodes 15 serve as electrical heaters. Electrical energy is provided by a power supply 240, located in the DP 200, and transmitted via wires and connectors 155, located in the DP 200 and cradle unit 20, to at least one heating electrode 15 which converts the electrical energy to heat. The power supply 240 may alternatively be located in the RP (not shown). Temperature can be controlled using variable resistors, and duration and quantity of the power supplied.

Figure 7B:
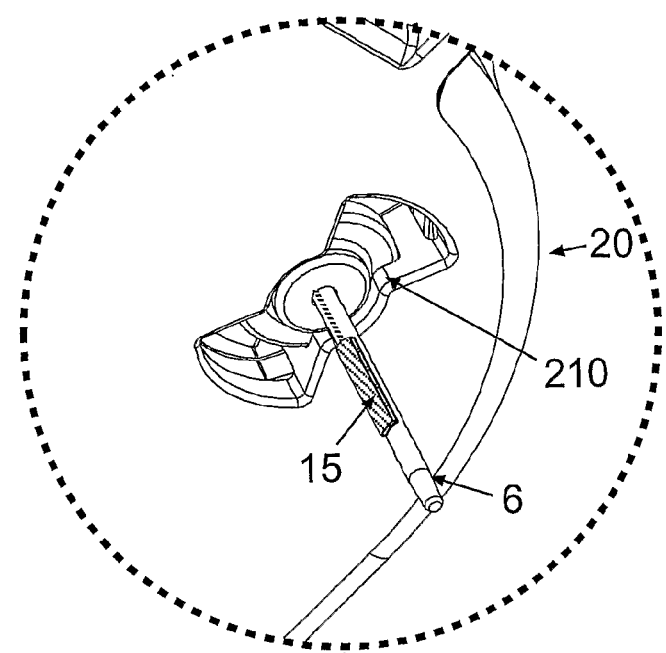
FIGS. 7a-7c illustrate the inferolateral aspect of the dispensing patch unit connected to the cradle unit, and the cannula coated with a heating electrode.
Figure 7A:
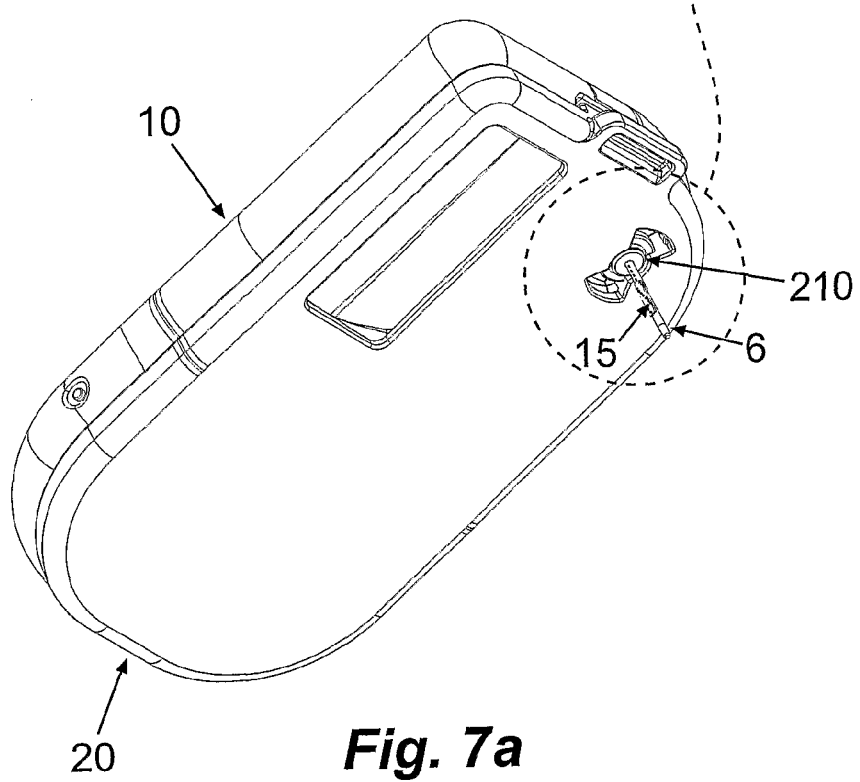
Figure 7C:
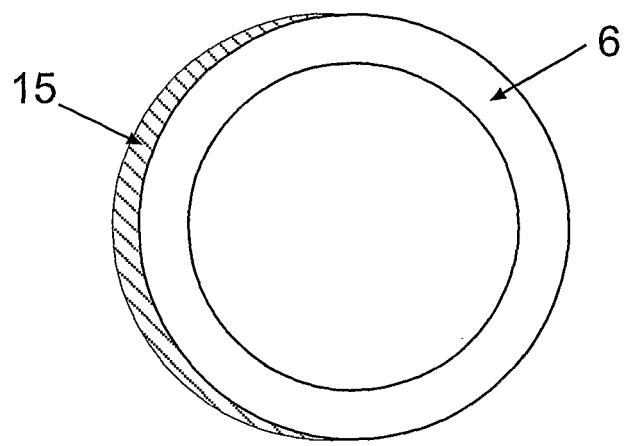

FIG. 7a illustrates the inferolateral aspect of the dispensing patch unit 10 connected to the cradle unit 20, and the cannula 6, coated with at least one heating electrode 15, that penetrates through a "well" 210 of the cradle unit. The well 210 is a protrusion that encircles a passageway enabling the insertion and placement of the cannula in a subcutaneous compartment of the user's body and rigidly anchoring the cannula. FIG. 7b is a magnification of the portion of FIG. 7a depicting the electrode 15 coated cannula 6 protruded through the well 210 of the cradle unit 20. FIG. 7c illustrates a transverse section of the cannula 6 and heating electrode 15. The electrode 15 in FIGS. 6a-c is limited to a partial length and circumference of the cannula.

Figure 8B:
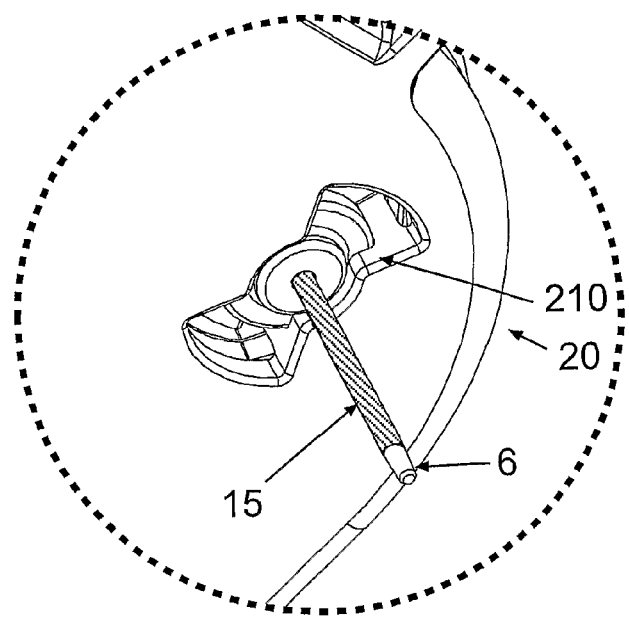
FIGS. 8a-8c illustrate another embodiment of the inferolateral aspect of the dispensing patch unit connected to the cradle unit, and the cannula coated with a heating electrode.
Figure 8A:
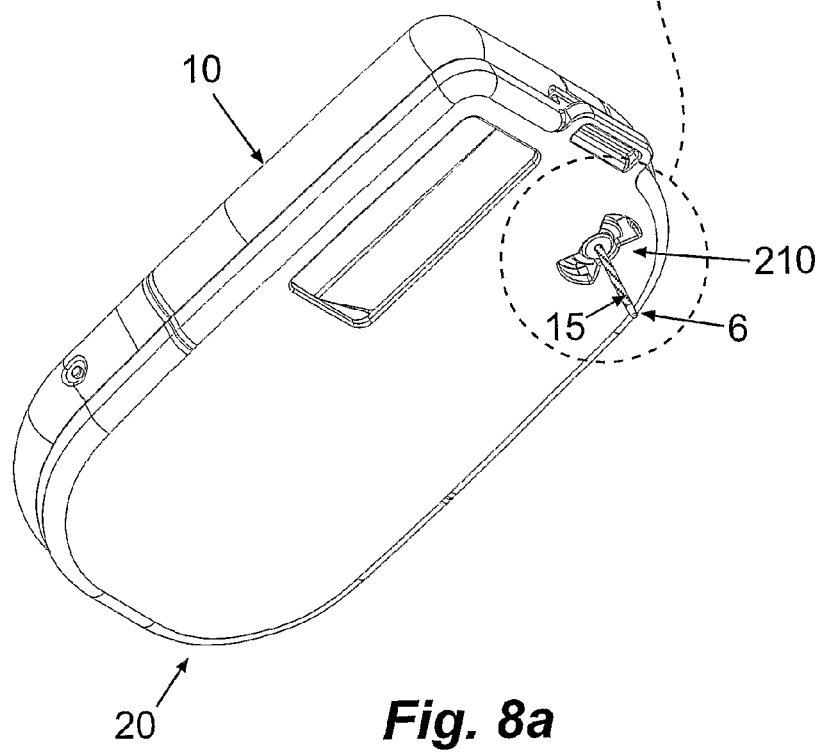
Figure 8C:
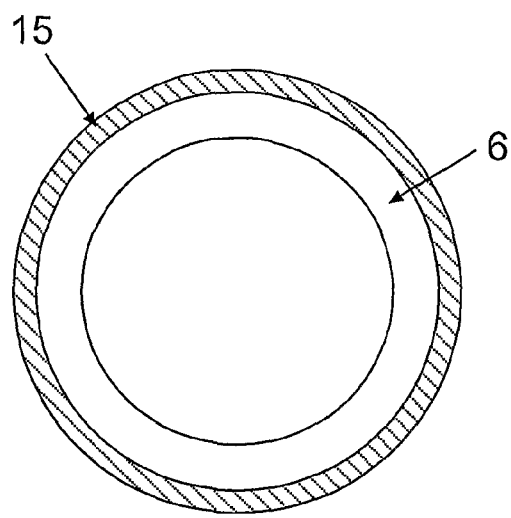

FIG. 8a illustrates the inferolateral aspect of another embodiment of the dispensing patch unit 10 connected to the cradle unit 20, and the cannula 6, coated with a heating electrode 15, penetrating through a well 210 of the cradle unit. FIG. 8b is a magnification of the portion of FIG. 8a depicting the electrode 15 coated cannula 6 protruded through the well 210 of the cradle unit 20. FIG. 8c illustrates a transverse section of the cannula 6 and circumferential heating electrode 15. The electrode 15 in FIGS. 7a-c covers the entire length and circumference of the cannula, thus allowing smoother insertion of the cannula through the well, and a larger and more symmetric area of local heating.

Figure 9:
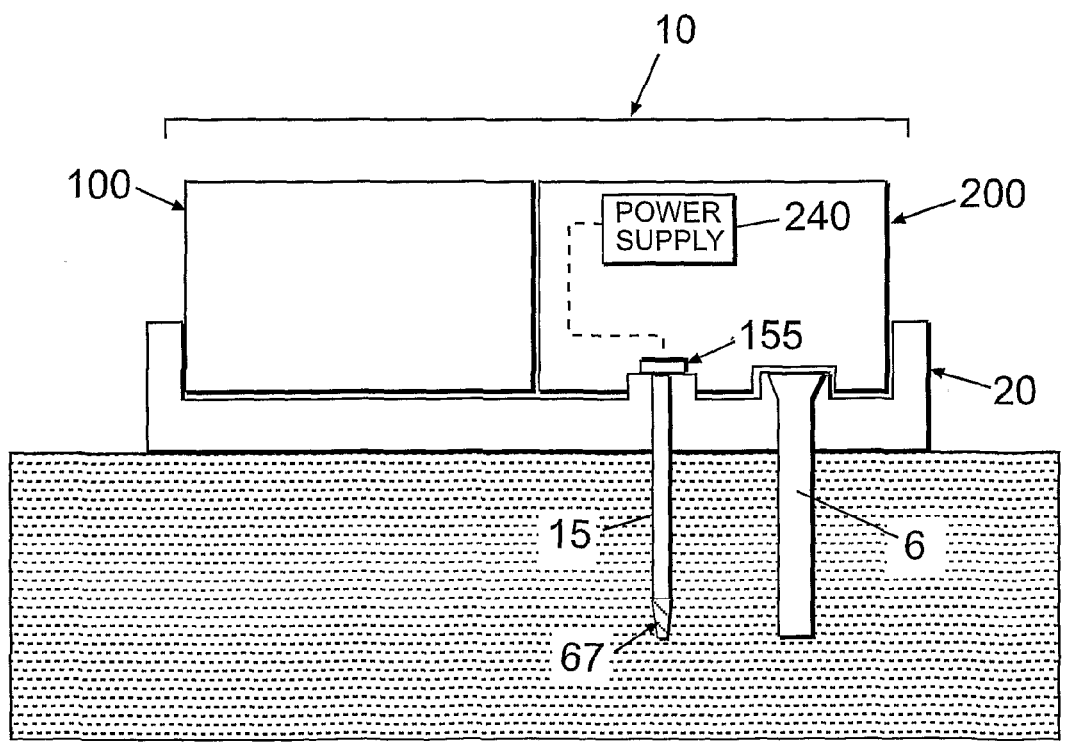
FIG. 9 shows a dispensing patch unit comprising a means for enhancing subcutaneous insulin absorption by local heating of the injection site by electrode/electrodes disposed on a designated subcutaneous element.

FIG. 9 shows a dispensing patch unit 10 comprising a means for enhancing subcutaneous insulin absorption by local heating of the injection site, wherein local heating is achieved by heating of at least one electrode 15 disposed on a designated subcutaneously located element 67. The dispensing patch unit 10 comprises proximal, subcutaneously located cannula for insulin delivery 6 and element 67 for mounting the heating electrode/electrodes 15 used for enhancing insulin absorption. Electrical energy is provided by a power supply 240, located in the DP 200, and transmitted via wires and connector 155 to the heating electrodes 15 which serve as electrical heaters which convert the electrical energy to heat. The power supply 240 may alternatively be located in the RP (not shown).

Figure 10B:
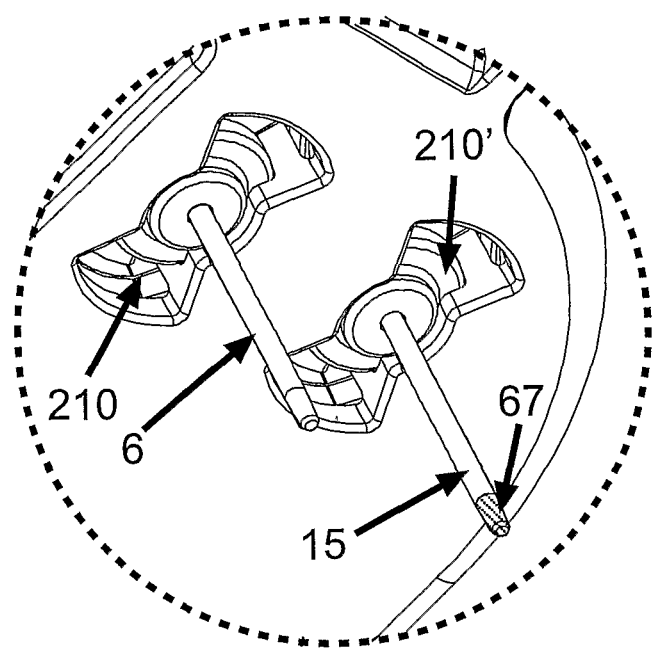
FIGS. 10a-10b illustrate the inferolateral aspect of a dispensing patch unit connected to a cradle unit, a drug delivery cannula, and a subcutaneous element with a heating electrode.
Figure 10A:
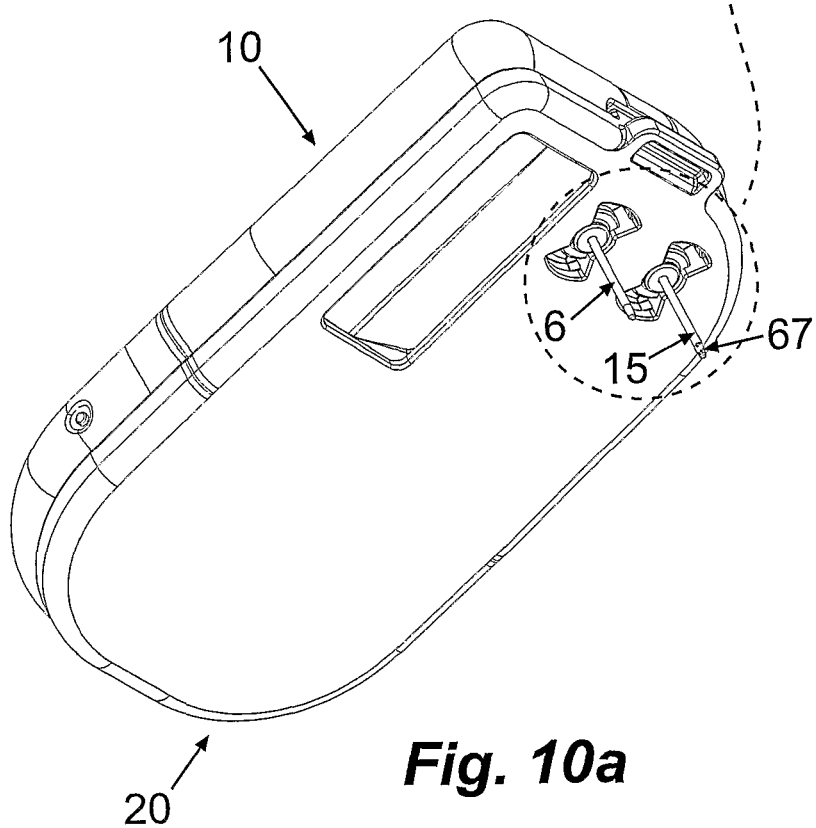

FIG. 10a illustrates the inferolateral aspect of the dispensing patch unit 10 connected to the cradle unit 20, the cannula 6 through which insulin is delivered, and the element 67 coated with at least one heating electrode 15. Both cannula 6 and element 67 penetrate through dedicated wells, 210 and 210' respectively. FIG. 10b is a magnification of the portion of FIG. 10a depicting electrode covered element 67 and cannula 6 penetrating through the bottom of the cradle unit.

Figure 11A:
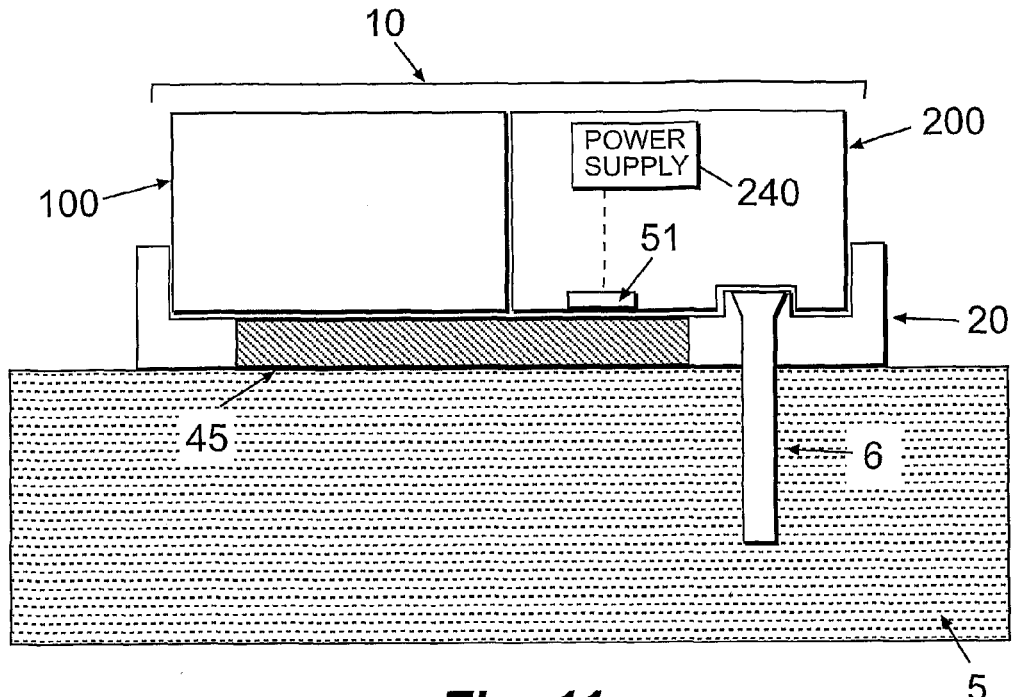
FIGS. 11a-11b show two embodiments of a dispensing patch unit comprising a means for enhancing subcutaneous insulin absorption by local transdermal heating of the injection site.
Figure 11B:
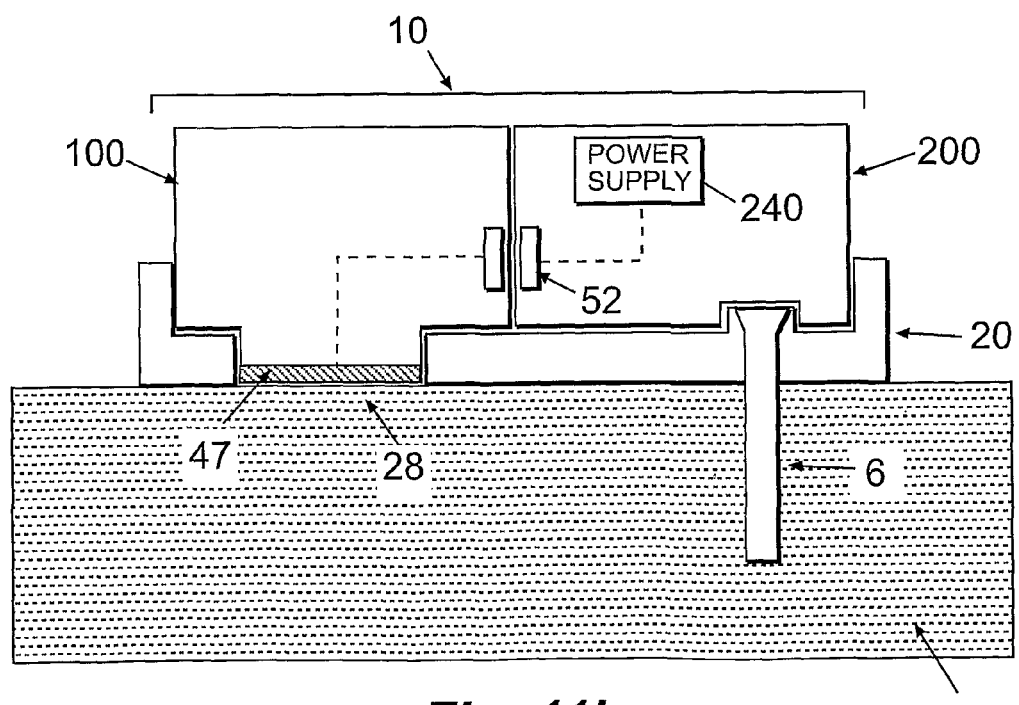

FIGS. 11a-b show two embodiments of a dispensing patch unit 10 comprising a means for enhancing subcutaneous insulin absorption by local transdermal heating of the injection site.

In FIG. 11a electrical energy is provided by a power supply 240, located in the DP 200, and transmitted via wires and connectors 51 to at least one heating plate 45 located in the cradle unit 20. The skin 5 located directly beneath the cradle unit is thus exposed to the heat generated by the heating plate 45.

The power supply 240 may alternatively be located in the RP (not shown).

In FIG. 11b the heating plate 45 is located in the RP 100. A cavity 28 in the cradle unit 20 located directly beneath the heating plate 47 provides better heat transfer from the heating plate 47 in the RP to the underlying skin 5. Wires and connectors 52 located in the RP 100 and in the DP 200 allow electrical energy transfer from the power supply 240 in the DP 100 to the heating plate 47 in the RP 100. Alternatively (not shown), the power supply is located in the RP. Alternatively (not shown) the heating plate is located in the DP 200 and the cavity in the cradle unit is aligned with the location of the heating plate in the DP.

Figure 12A:
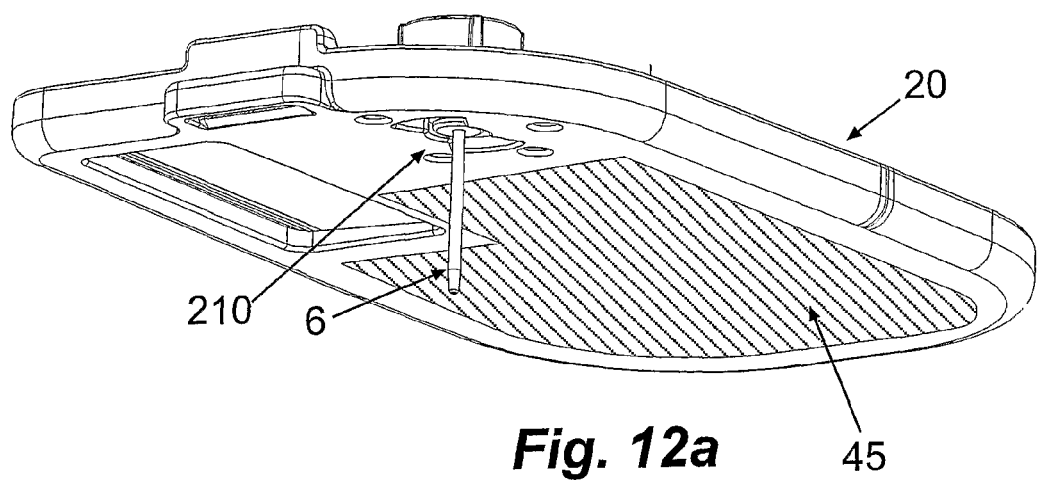
FIGS. 12a-12b illustrate the inferolateral aspect of a cradle unit comprising a heating electrode which serves as a means for enhancing subcutaneous insulin absorption by local transdermal heating of the injection site.
Figure 12B:
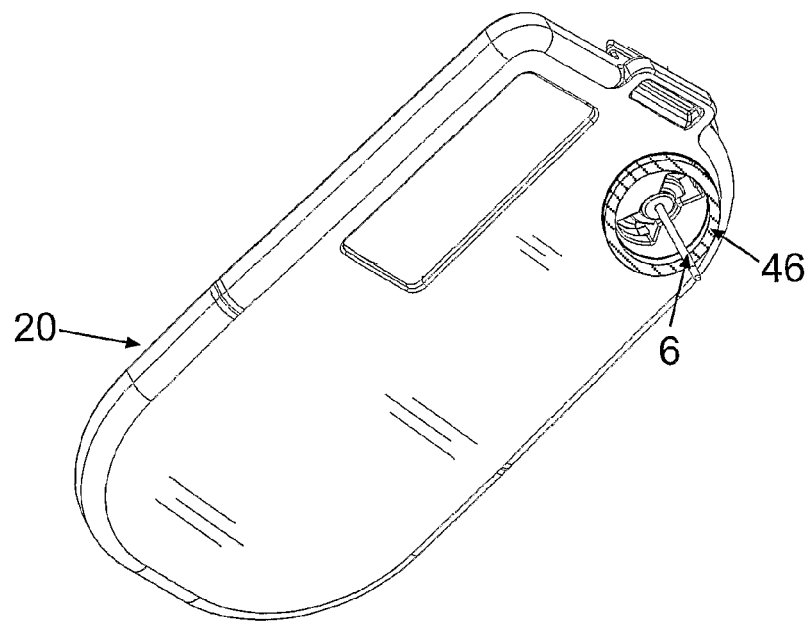

FIGS. 12a-b illustrate the inferolateral aspect of a cradle unit 20 comprising a heating electrode 45 which serves as a means for enhancing subcutaneous insulin absorption by local transdermal heating of the injection site. In FIG. 12a the heating plate covers a relatively large proportion of the bottom surface of the cradle unit. In FIG. 12b, the heating plate 46 is circumferential to the cannula 6 that penetrates through the well of the cradle unit 20. Such a rounded heating plate provides annular, symmetrical heat distribution around the cannula 6.

Figure 13A:
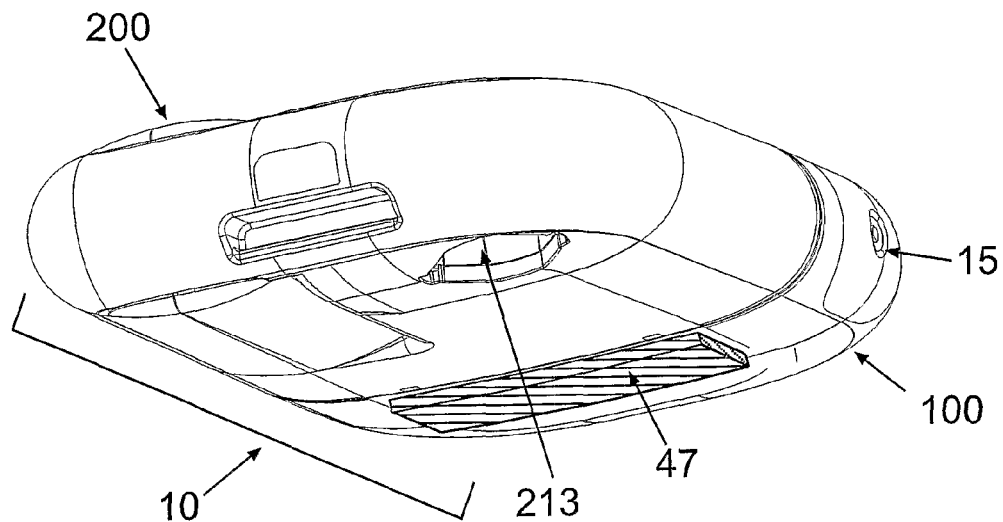
FIGS. 13a-13b illustrate inferolateral aspect of a dispensing patch unit comprising a heating plate in the Reusable Part of the dispensing patch (RP), and a cradle unit 20 with an opening aligned with the RP heating plate.
Figure 13B:
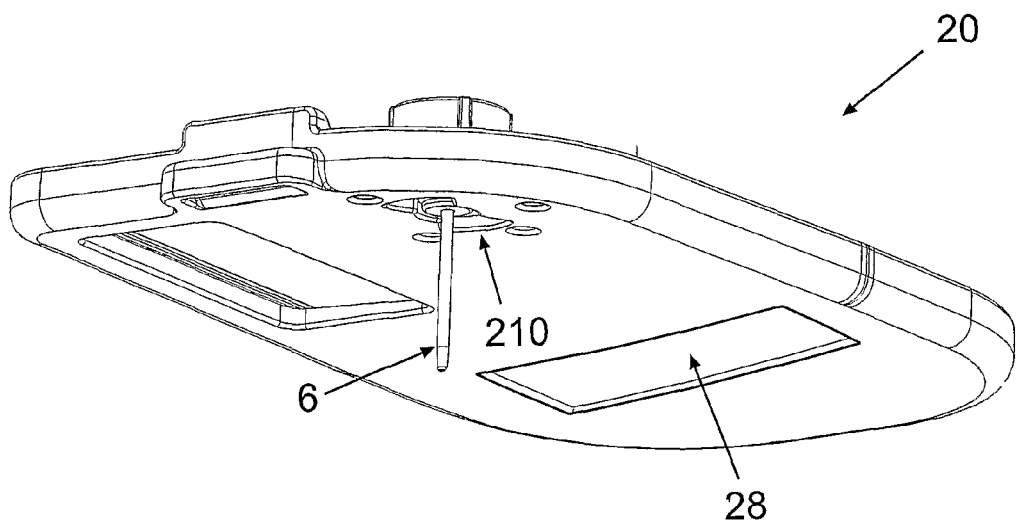

FIG. 13a illustrates the inferolateral aspect of a dispensing patch unit 10 comprising a heating plate 47 in the RP 100. FIG. 13b illustrates the cradle unit 20 with a opening 28 aligned with the expected location of the heating plate in the RP, once the patch unit is connected to the cradle unit.

Figure 14:
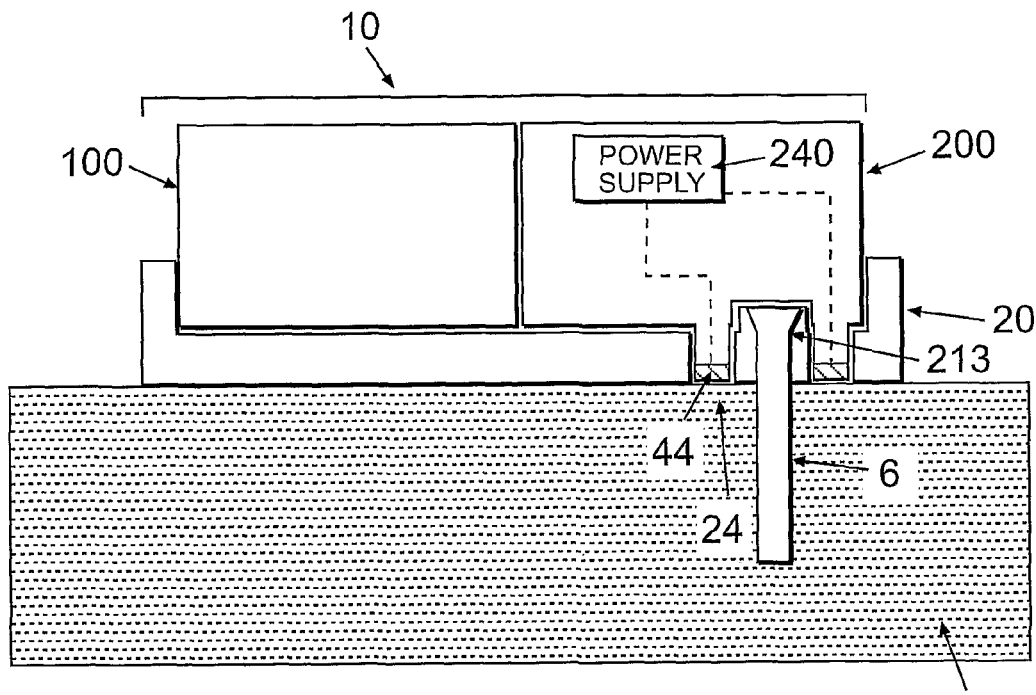
FIG. 14 illustrates another embodiment of a dispensing patch unit comprising a means for enhancing subcutaneous insulin absorption by local transdermal heating of the injection site.

FIG. 14 illustrates another embodiment of a dispensing patch unit 10 comprising a means for enhancing subcutaneous insulin absorption by local transdermal heating of the injection site. The heating plate 44 in FIG. 14 is arranged concentrically around the outlet port 213 of the DP 200. Such a rounded heating plate provides annular, symmetrical heat distribution around the cannula 6 through which the insulin is delivered. Electrical energy transfer from the power supply 240 in the DP 100 to the heating plate 44 by virtue of electrical wires. Alternatively (not shown), the power supply is located in the RP, and the electrical energy is transferred via wires and connectors between the RP and the DP.

An opening 24 in the cradle unit 20 located directly beneath the heating plate 44 provides better heat transfer from the RP to the underlying skin 5. The opening 24 in the cradle unit may be segmented as to hold the base of the cradle unit and the well in one piece.

Figure 15A:
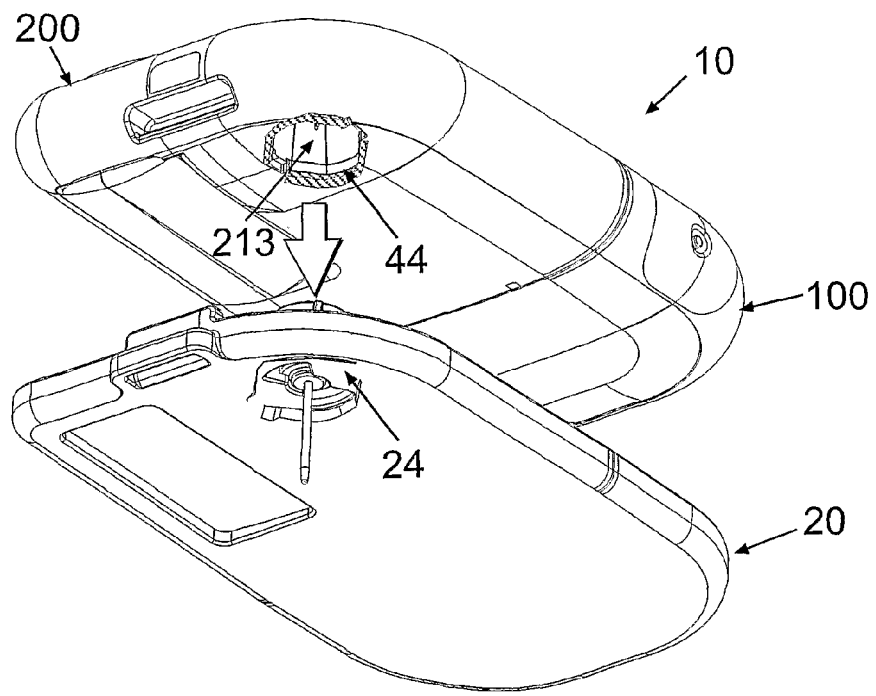
FIGS. 15a-15b show the inferolateral aspect of the patch unit that contains an annular heating plate, and a cradle unit with an opening aligned with the patch unit heating plate.
Figure 15B:
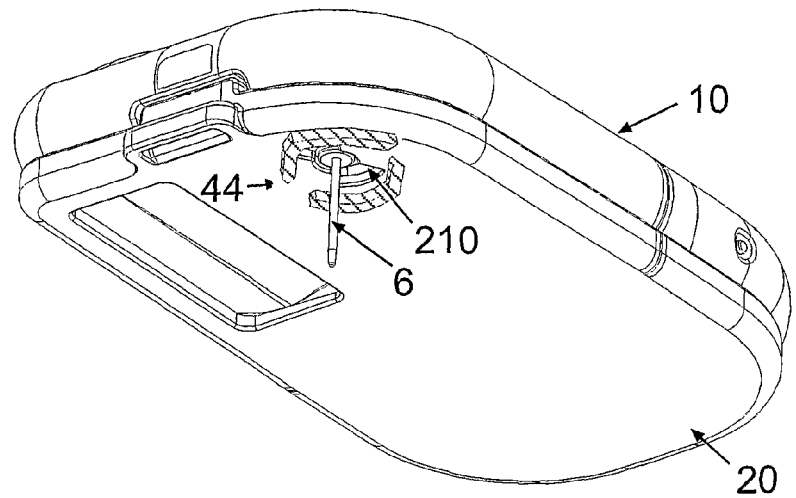

FIGS. 15 a-b show the inferolateral aspect of the patch unit 10 with the annular heating plate 44 around the outlet port 213, and the cradle unit 20 with the dedicated segmented opening 24 aligned with the heating plate in the patch unit 10. FIG. 15a shows the cradle unit 20 and patch unit 10 disconnected. FIG. 15b shows the two parts connected. The heating electrode 44 is exposed by virtue of the segmented opening 24 in the cradle unit 20 once the two parts are assembled.

Figure 16A:
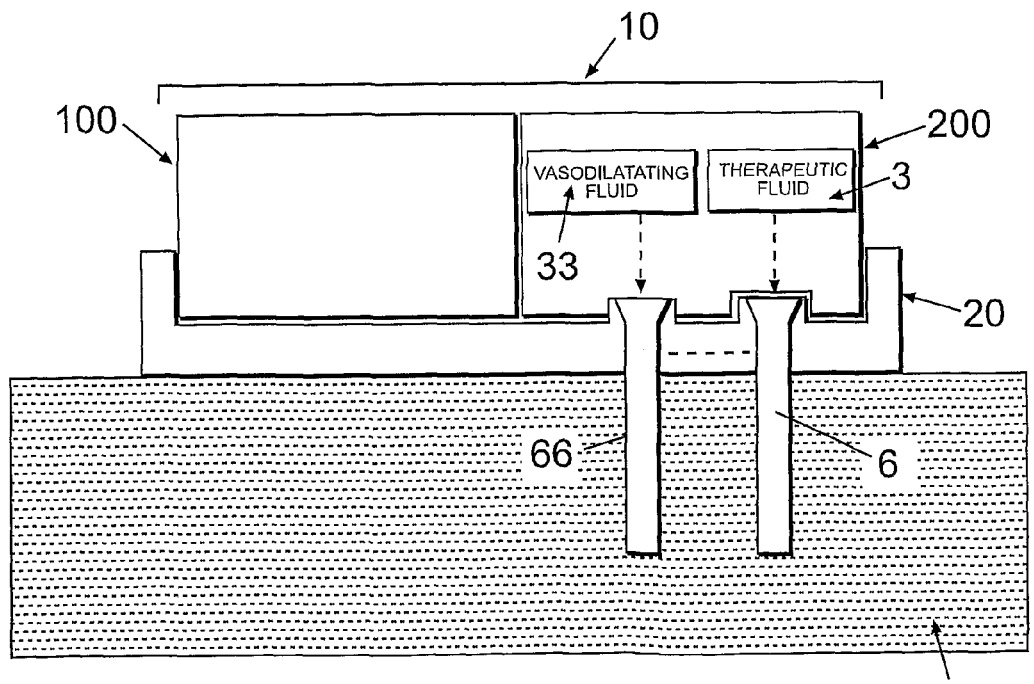
FIGS. 16a-16b show two different embodiments of a dispensing patch unit provided with means for enhancing subcutaneous insulin absorption by administration of a vasodilating pharmacologic agent.
Figure 16B:
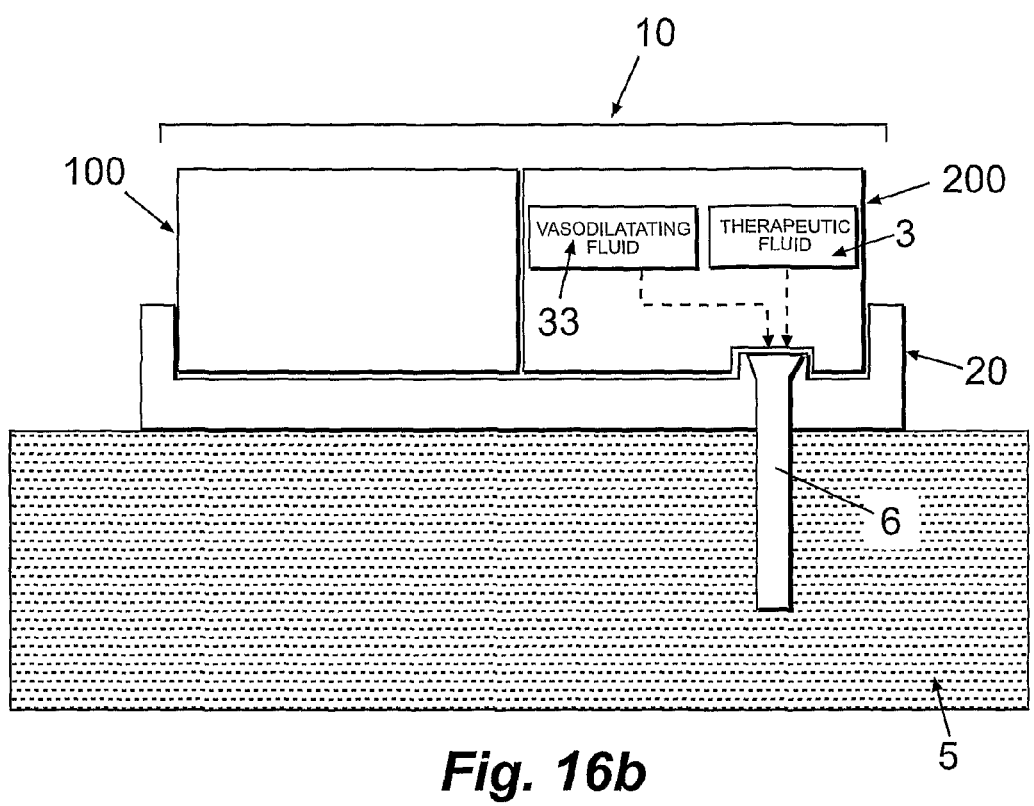

FIGS. 16a-b show two different embodiments of a dispensing patch unit 10 provided with the capability of enhancing subcutaneous insulin absorption by concomitant administration of a vasodilating pharmacologic agent (e.g. nitroglycerin, nitroprusside, histamine, PDE5 inhibitor). The vasodilating pharmacologic agent is alternatively delivered prior to, or immediately after, the administration of the therapeutic fluid (e.g. insulin). The insulin and the vasodilatory agent have different reservoirs 3 and 33 respectively, and different delivery tubes.

In FIG. 16a the vasodilatory agent is delivered via a dedicated cannula 66, and the dispensing patch unit 10 comprises two proximal, subcutaneously located cannulae; one for insulin delivery 6 and one for vasodilatory agent delivery used for enhancing insulin absorption. In FIG. 16b the vasodilatory agent and the insulin are delivered via the same cannula 6. The dose, rate, and timing of delivery of both pharmaceutical agents (i.e. insulin, vasodilator agent) can be controlled by the user.

Figure 17B:
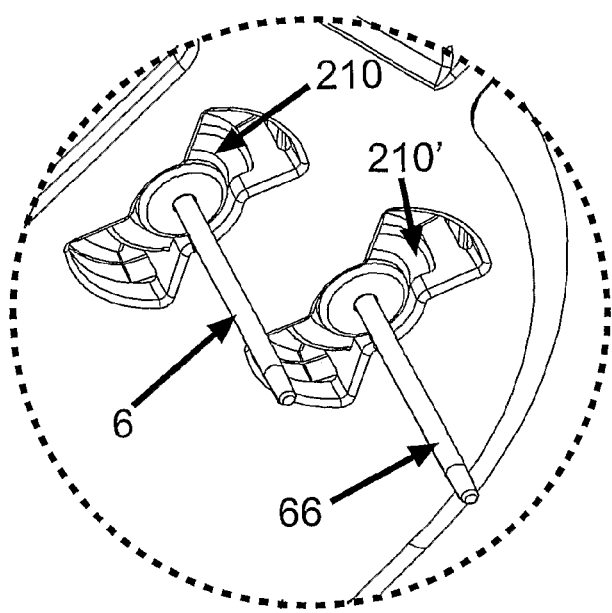
FIGS. 17a-17b illustrate the inferolateral aspect of the dispensing patch unit connected to the cradle unit, the cannula through which insulin is delivered, and the cannula through which a vasodilatory agent is delivered.
Figure 17A:
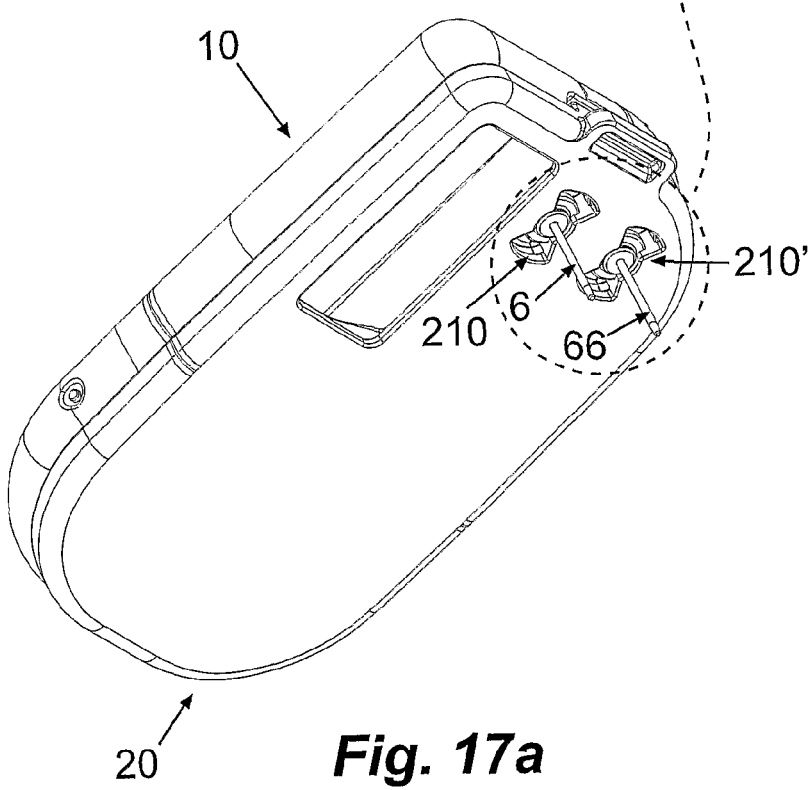

FIG. 17a illustrates the inferolateral aspect of the dispensing patch unit 10 connected to the cradle unit 20, the cannula 6 through which insulin is delivered, and the cannula 66 through which a vasodilatory agent is delivered. Both cannulae 6, 66 penetrate through dedicated wells, 210 and 210' respectively. FIG. 17b is a magnification of the portion of FIG. 17a depicting the two cannulae 6, 66 penetrating through the bottom of the cradle unit 20.

Figure 18A:
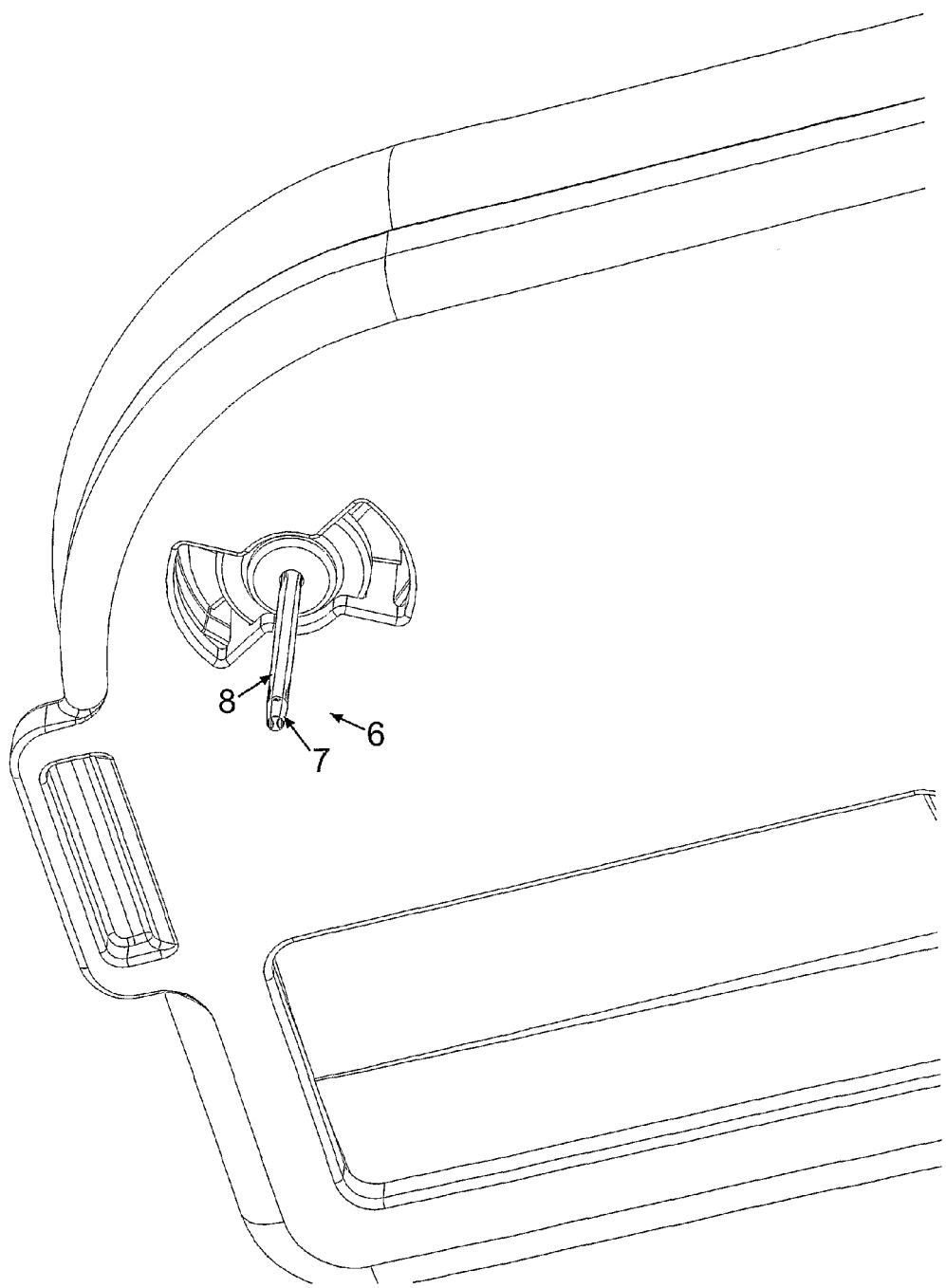
FIGS. 18a-18b illustrate another embodiment in which the insulin and the vasodilatory agent are delivered through one double lumen cannula.
Figure 18B:
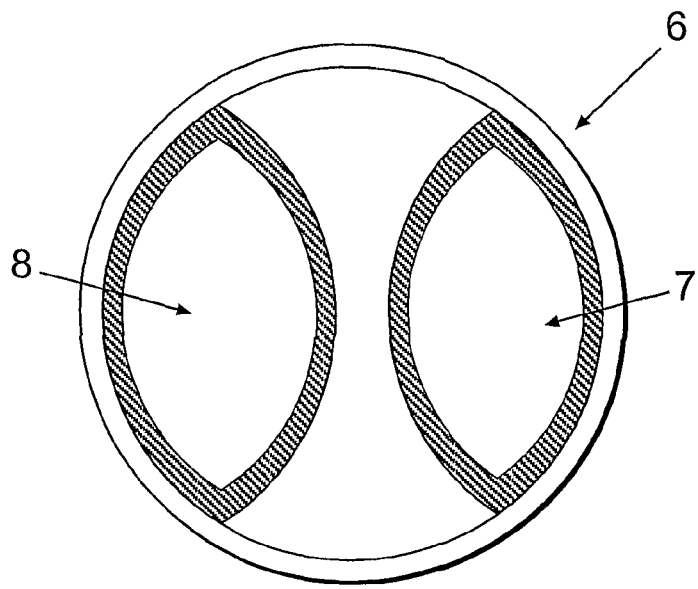

FIG. 18a illustrates another embodiment in which the insulin and the vasodilatory agent are delivered through one double lumen cannula 6. One lumen 7 is dedicated for insulin delivery and the other lumen 8 is dedicated for delivery of a vasodilatory agent. FIG. 18b is a cross section of the double lumen 7, 8 cannula 6.

Figure 19:
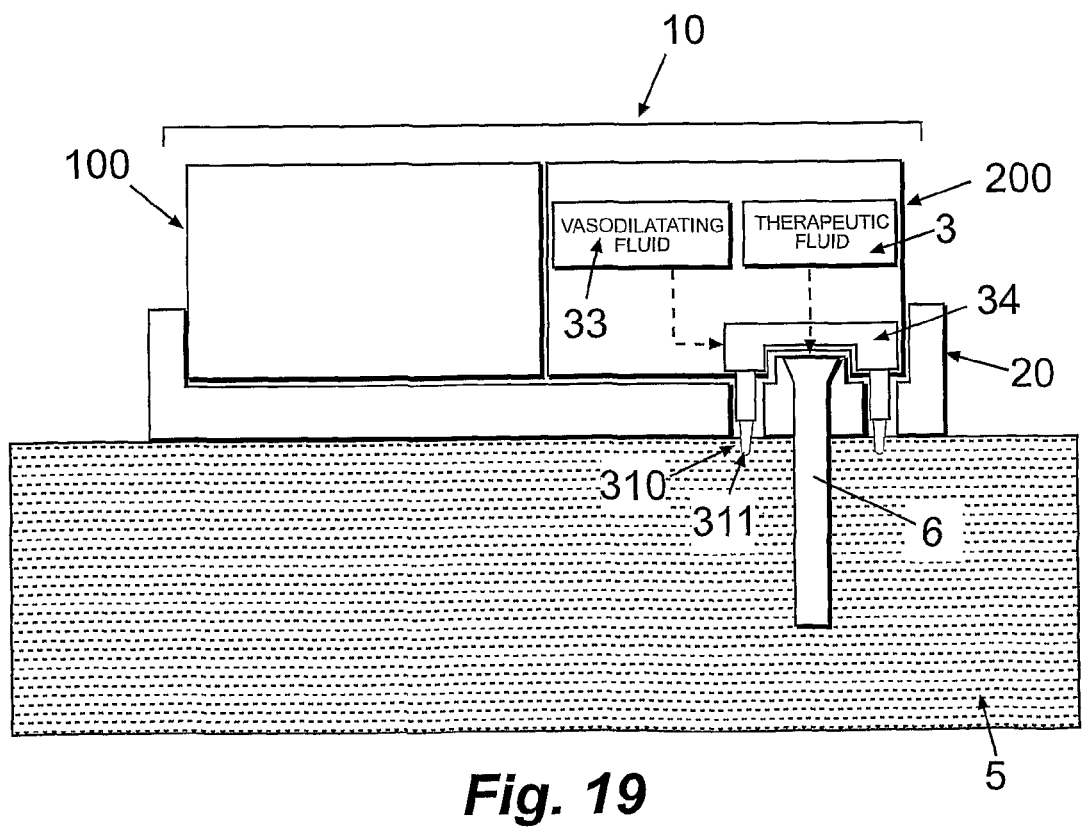
FIG. 19 shows a dispensing patch unit provided with means for enhancing subcutaneous insulin absorption by administration of a vasodilating pharmacologic agent via a dedicated array of microneedles.

FIG. 19 shows a dispensing patch unit 10 provided with the capability of enhancing subcutaneous insulin absorption by administration of a vasodilating pharmacologic agent (e.g. nitroglycerin, nitroprusside, histamine, PDE5 inhibitor) via a dedicated array of microneedles. The therapeutic agent (e.g. insulin) and the vasodilatory agent have different reservoirs, 3 and 33 respectively, and different delivery tubes. The insulin reservoir 3 is connected to a cannula 6 and the reservoir containing the vasodilatory agent 33 is connected by a secondary reservoir 34 which is in direct connection with an array of microneedles 311. According to the embodiment, the microneedles are arranged concentrically around the cannula 6, and the secondary reservoir 34 is a ringed shape tube and the microneedles 311 extend downward therefrom. The cradle unit 20 comprises dedicated micro-openings 310 through which the microneedles 311 penetrate. According to another embodiment (not shown) the cradle unit comprises a segmented hollow opening through which the microneedles can easily penetrate (i.e., opening in the cradle unit for the entire array of microneedles rather than micro-openings for each microneedle). The microneedles 311 penetrate only the outermost layer of skin 5 that contains no nerve endings, and thus avoid causing pain during insertion and at the same time avoid the mechanical barrier presented by the outer layer of the epidermis the stratum corneum.

Figure 20A:
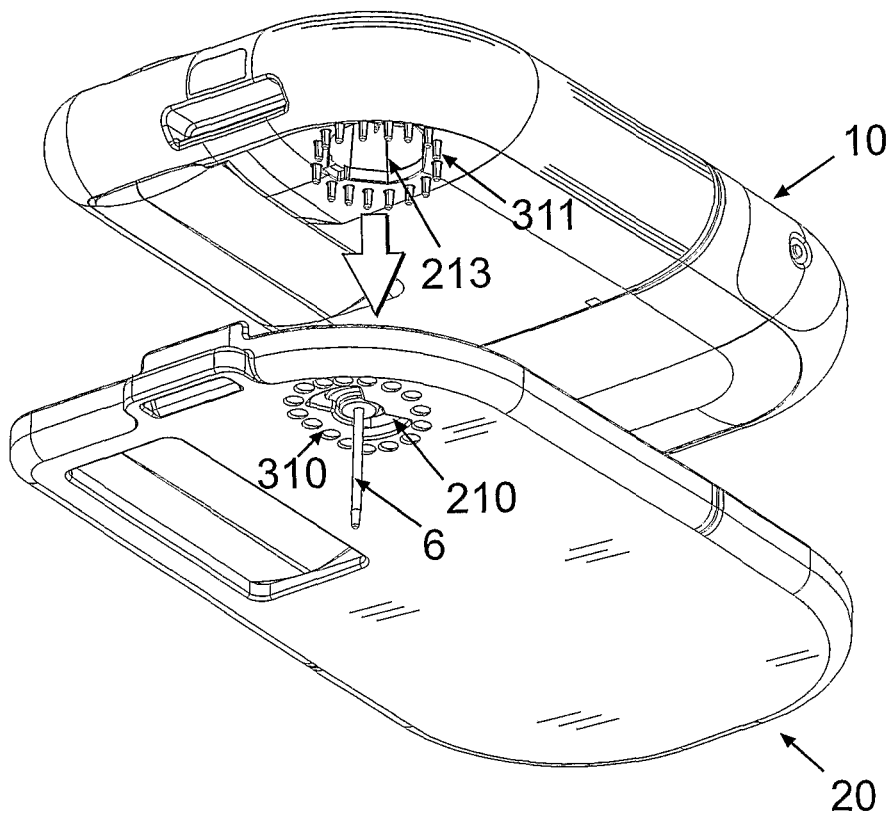
FIGS. 20a-20b show the inferolateral aspect of the patch unit with an array of micro-needles arranged around the outlet port, and a cradle unit that contains dedicated openings aligned with the microneedles in the patch unit.
Figure 20B:
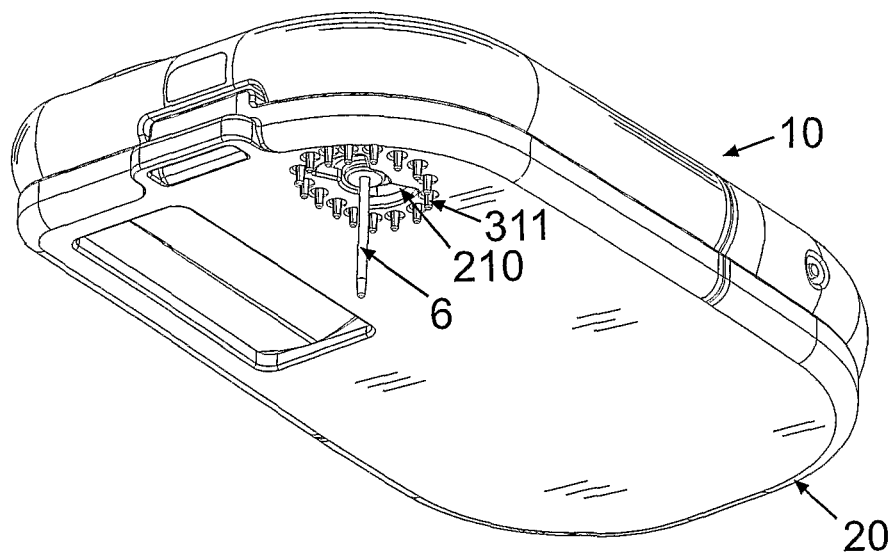

FIGS. 20a-b show the inferolateral aspect of the patch unit 10 with the array of microneedles 311 arranged around the outlet port 213, and the cradle unit 20 with the dedicated openings 310 arranged around the well 210 and aligned with the microneedles 311 in the patch unit 10. FIG. 20a shows the cradle unit 20 and patch unit 10 disconnected. FIG. 20b shows the two parts connected. The microneedles 311 penetrate through the openings 310 once the two parts are assembled.

Figure 21:
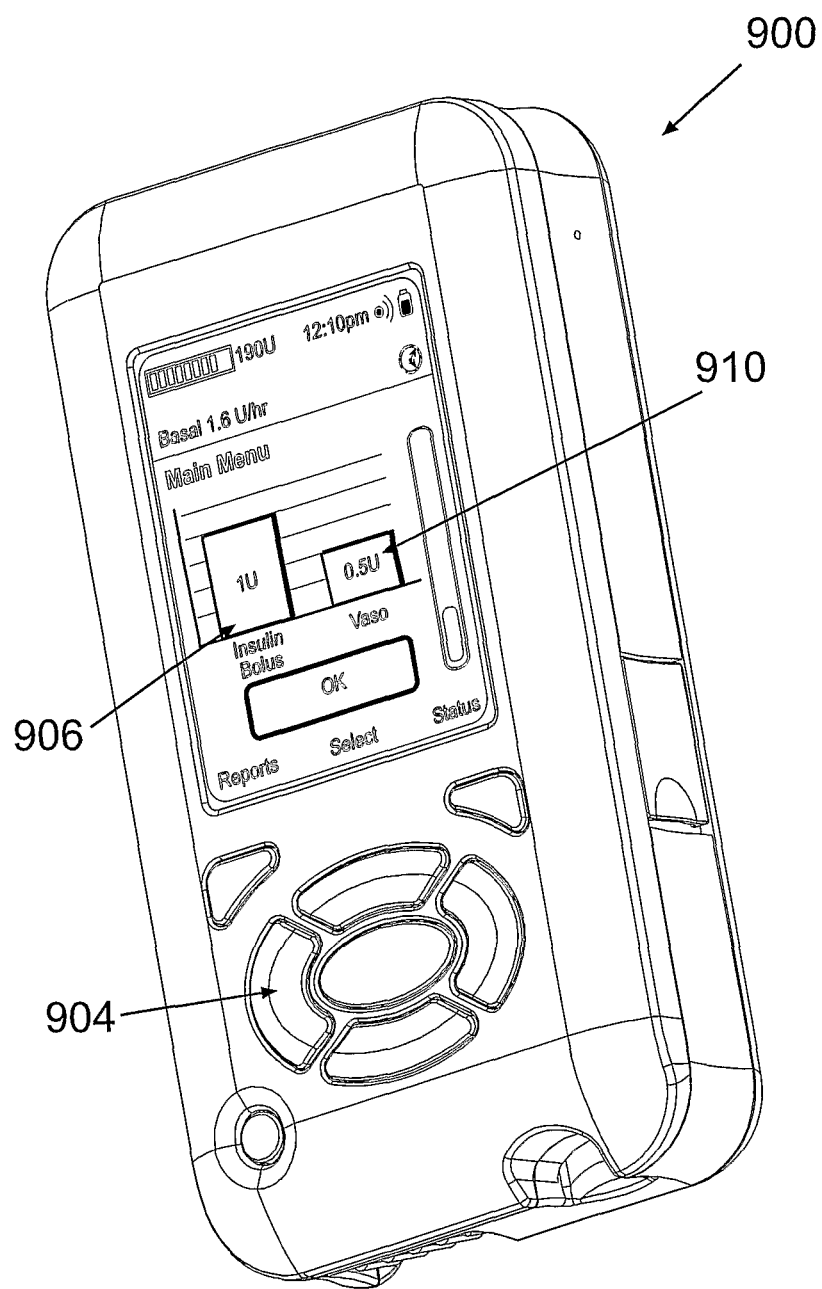
FIG. 21 shows the remote control unit with GUI showing data of insulin dose administration and vasodilatory agent administration.

FIG. 21 shows the remote control unit 900, with navigating buttons 904, showing data of insulin bolus dose administration 906 and vasodilatory agent administration 910 in an insulin delivery device (not shown) provided with the capability of enhancing subcutaneous insulin absorption by administration of a vasodilating pharmacologic agent.

Figure 22:
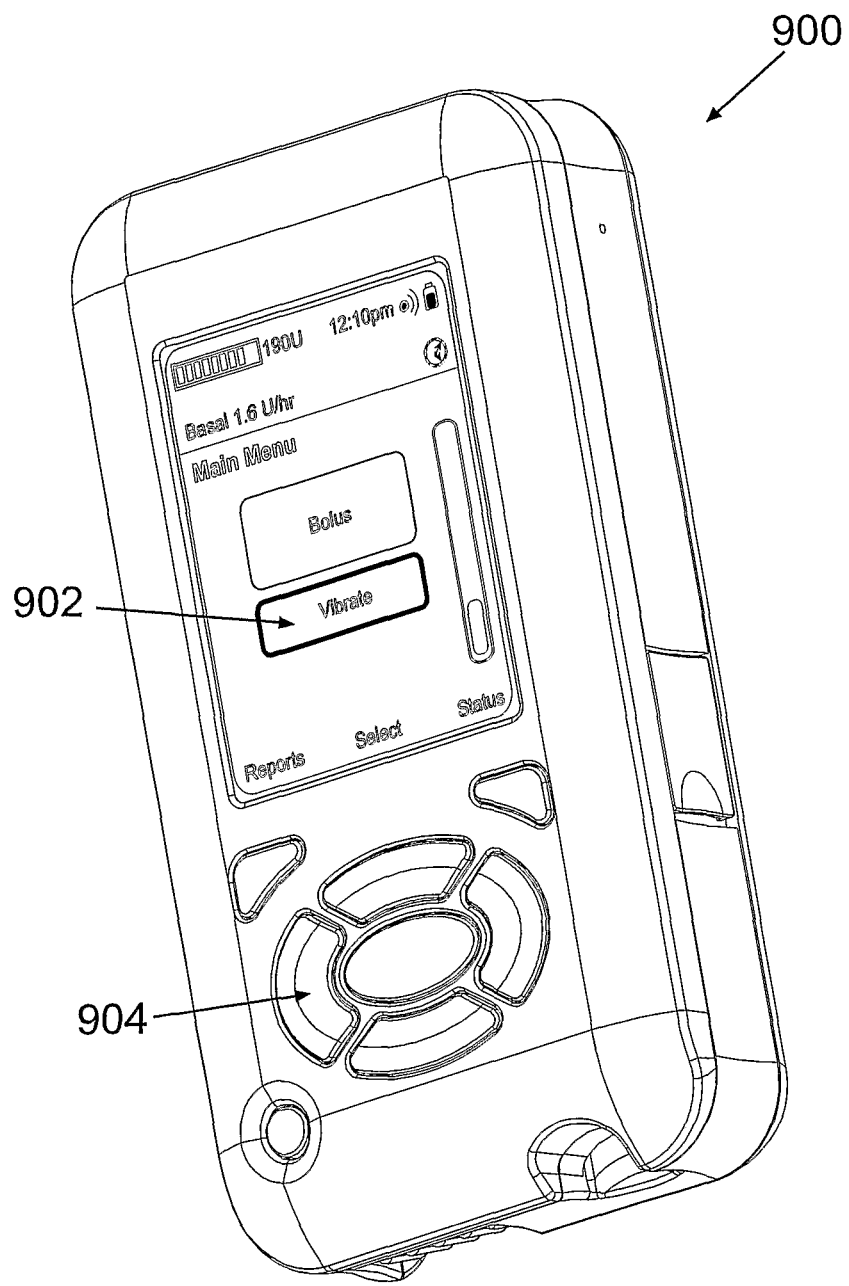
FIG. 22 shows the remote control unit with GUI indicating vibration as a means for achieving local heating for enhancement of therapeutic fluid absorption.

According to one embodiment of the invention, local heating of the subcutaneous tissue can be obtained by local high frequency vibration, as can be seen in the GUI of the remote control unit 900 illustrated in FIG. 22. The 'vibrate' option is indicated with numeral 902. According to one such embodiment, vibration can be achieved by ultrasound acoustic energy—a modality commonly used in physiotherapy to achieve deep tissue warming.

Figure 23A:
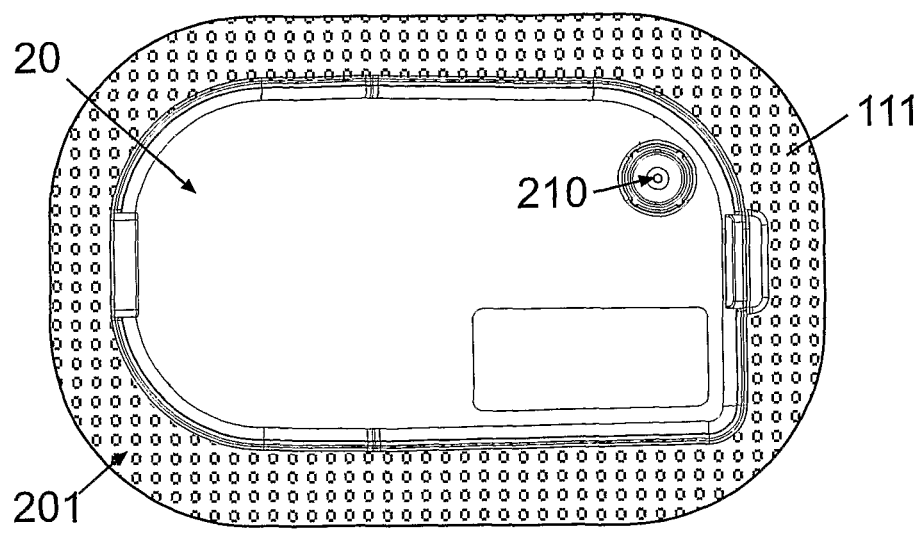
FIGS. 23a-23b illustrate a transdermal patch unit that can deliver at least one local vasodilator agent.
Figure 23B:
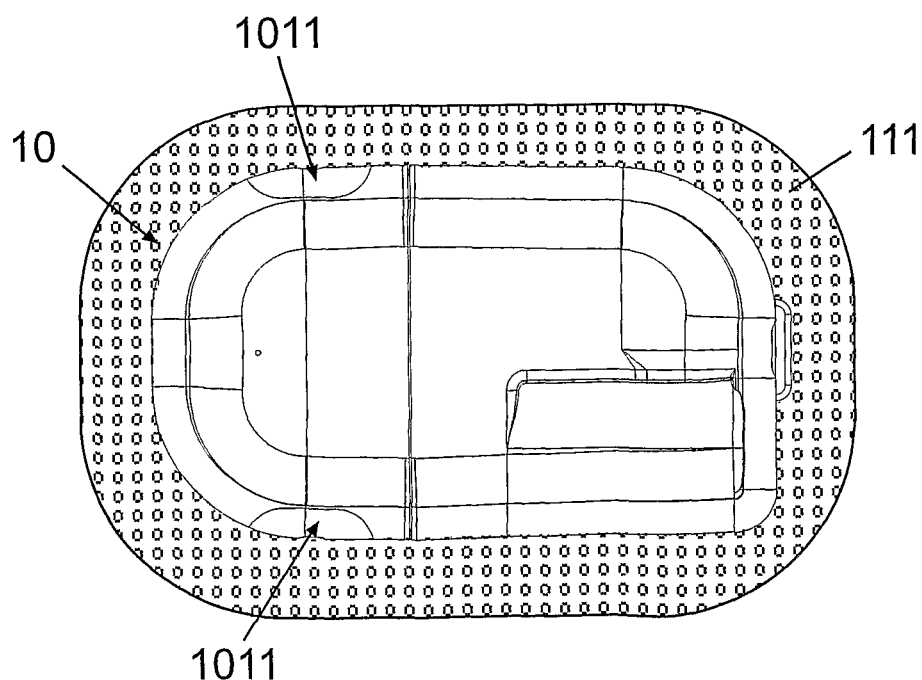

FIGS. 23a and 23b illustrate a transdermal patch unit that can deliver at least one local vasodilator agent. Transdermal patches are commonly used to deliver pharmaceutical materials percutaneously. Transdermal patches are generally layered structures, with the skin-facing layer comprising an adhesive having microholes. Above this adhesive layer is a medication containing layer, and a waterproof cover layer is generally provided. The adhesive serves to attach the patch to the skin and the medication in the central layer is provided to the skin through the microholes in the adhesive layer. Slow and controlled release of the medication may be achieved by such transdermal patches.

FIG. 23a shows the cradle unit 20 that comprises, at least in part, an adhesive layer 111 to securely attach the cradle unit 20 to the patient's skin. The adhesive 111 should be biocompatible (e.g. does not stimulate irritation) and comfortable to the patient without disturbing his/her diurnal routine. Before adhesion a protective peelable cover layer (not shown) should be removed from the adhesive. According to the embodiment, a vasodilator containing layer may be disposed on the adhesive layer 111. The adhesive layer 111 may contain microholes 201. The distribution of the microholes 201 on the adhesive layer may determine the skin area affected by the drug. According to one embodiment, the microholes can be located only in the immediate circumference of the cannula through which the insulin is delivered. The transdermally delivered vasodilator, contained in the patch unit, may be any one or more of the known in the art transdermally delivered vasodilators such as nitroglycerine, papaverine, and prostaglandin E1. According to one embodiment, transdermal vasodilatation using 10 milligrams of phentolamine mesylate dissolved in 0.23 mL of alcohol may be used, as detailed in U.S. Pat. No. 6,007,836 which describes a system for producing and maintaining male erection by transdermal administration of a vasodilating agent. FIG. 23b illustrates the patch unit 10 connected to the cradle unit with vasodilator bound adhesives 111.

Figure 24A:
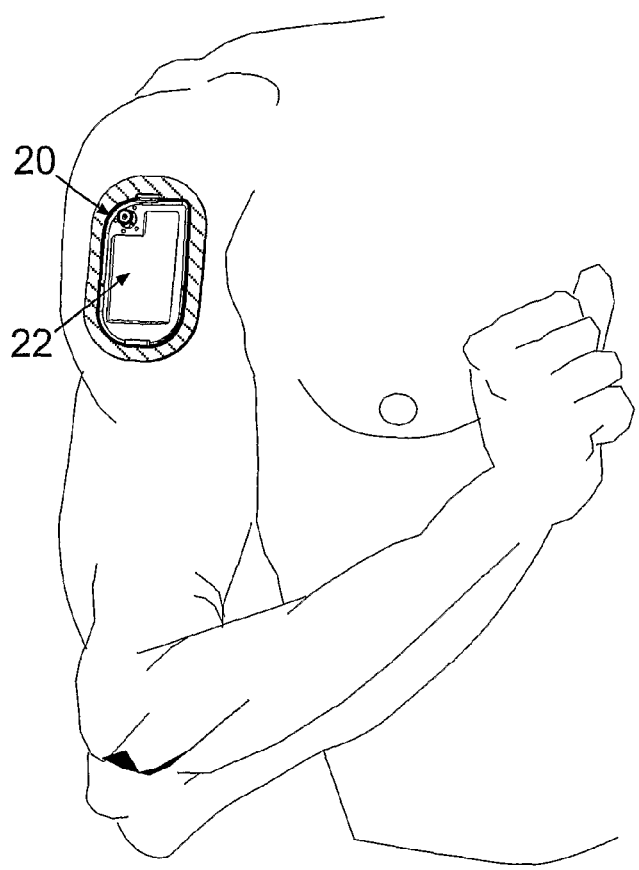
FIGS. 24a-24d illustrate topical administration of a vasodilatory agent as a means for enhancing insulin absorption.

FIGS. 24a-24d illustrate topical administration of a vasodilatory agent as a means for enhancing insulin absorption. In FIG. 24a, the cradle unit 20 attached to the user's skin is shown to comprise a cavity 22 through which the skin is exposed.

Figure 24B:
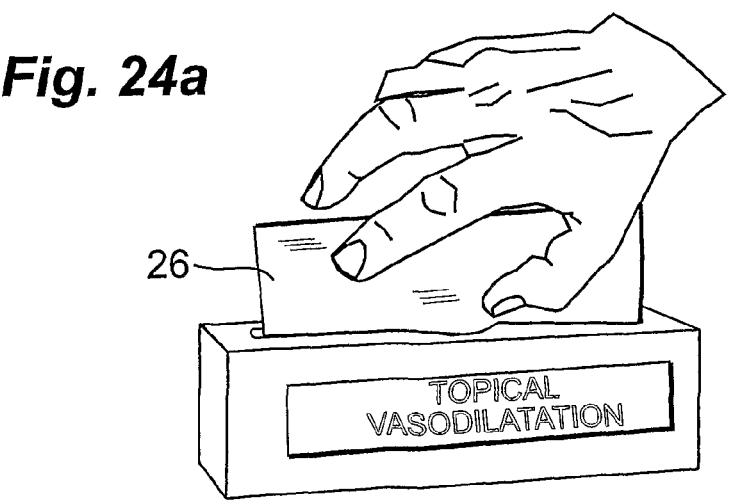
Figure 24C:
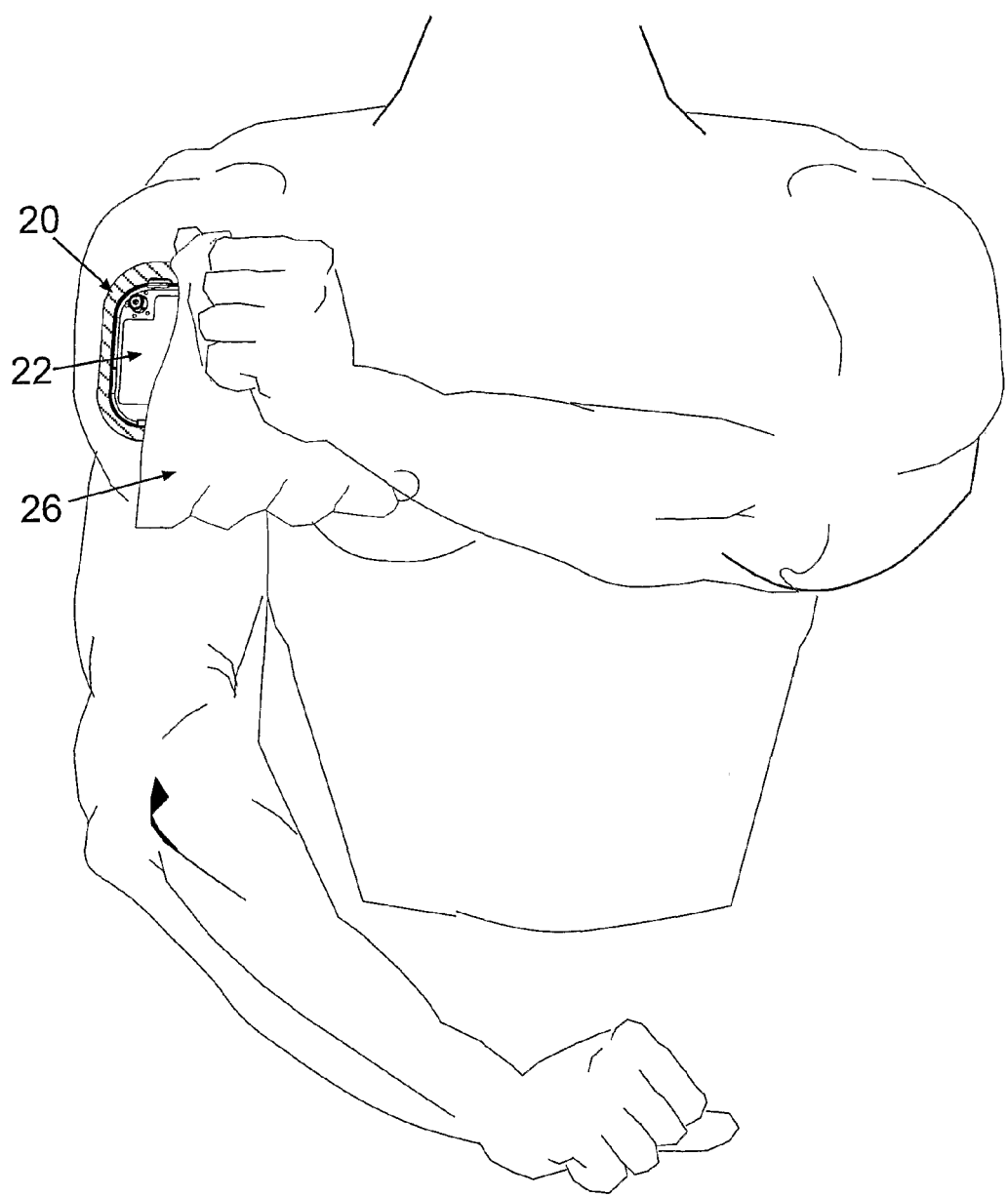
Figure 24D:
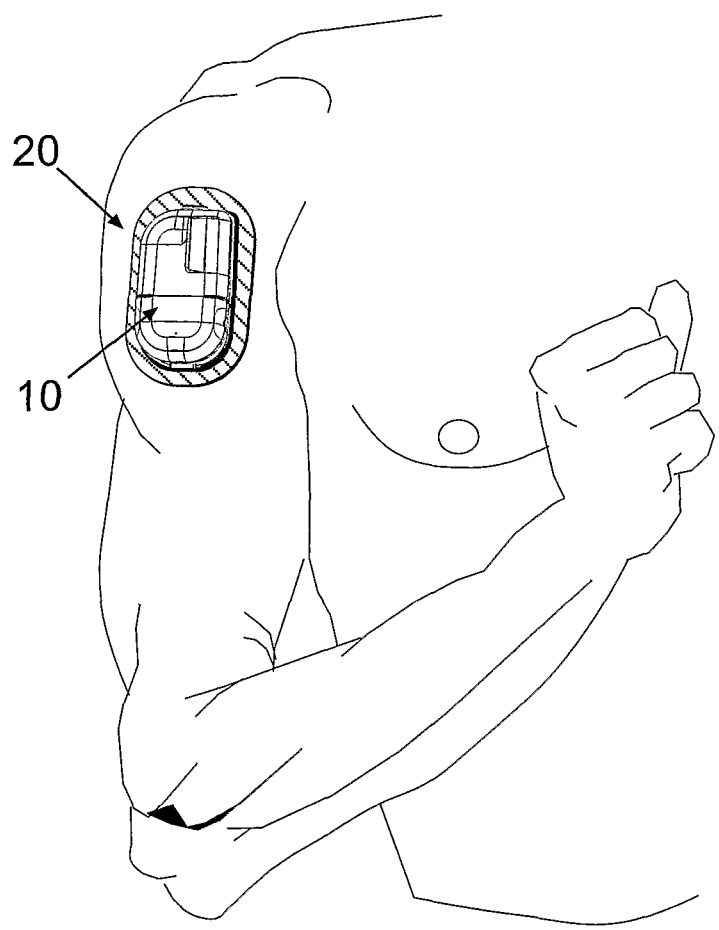

FIG. 24b shows wipes 26 comprising a topical vasodilatory agent. FIG. 24c shows the user topically applying the vasodilatory agent 26 to the exposed skin, in the vicinity of the cannula, showing through the cradle unit 20. FIG. 24d shows the patch unit 10 reconnected to the cradle unit 20 after topical application of a vasodilating agent. The user may disconnect the patch from the cradle unit 20 and apply the topical vasodilator agent (possibly using the wipes depicted in FIG. 24b) only before a bolus is administered.

FIGS. 25a-d shows four different embodiments of a dispensing patch unit 10 comprising a component capable of enhancing subcutaneous insulin absorption by current application. According to one such embodiment, an electrical charge of 2-15 mC is applied. According to one embodiment, a segmented current application is applied. A segmented current application results in a peak vasodilatation superior to the one observed following a current of comparable total charge delivered all at once (Journal of Physiology 2002, 540(1), 261-269). The vascular response to galvanic current application is suggested to rely on an axon reflex and neurogenic inflammation with either anodal or cathodal current. The axon reflex-related cutaneous vasodilatation relies on the local release, from primary afferent fibers, of neural mediators such as calcitonin gene-related peptide, substance P, and prostaglandin (Am J Physiol Heart Circ Physiol 2005, 288: 668-673)

Figure 25A:
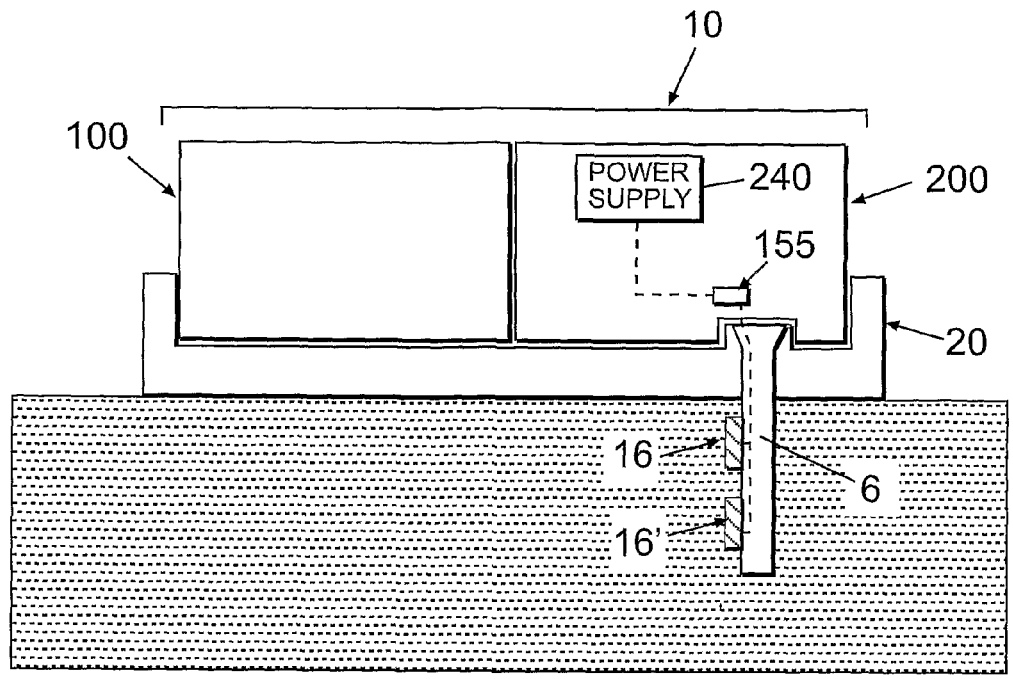
FIGS. 25a-25d show four different embodiments of a dispensing patch unit 10 comprising a component capable of enhancing subcutaneous insulin absorption by electrical current application.
Figure 25B:
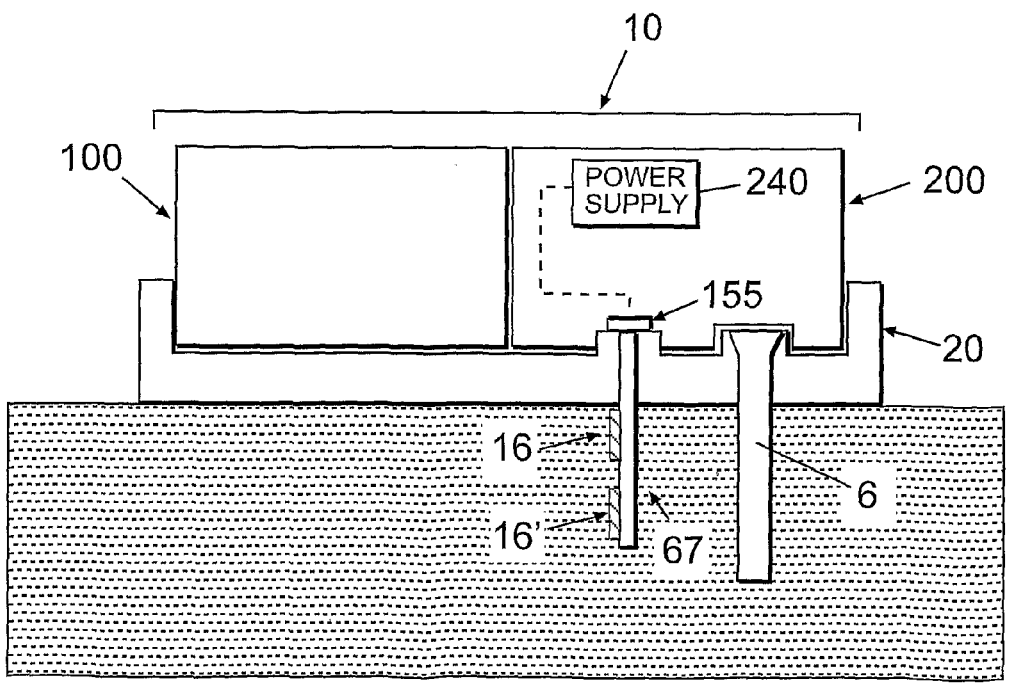

In FIG. 25a-b local vasodilation is achieved by applying the current directly in the subcutaneous tissue by virtue of at least two conduct electrodes 16 and 16' disposed on the surface of a subcutaneously inserted cannula or probe.

In FIG. 25a the conductive electrodes 16 and 16' are disposed on the same cannula through which the therapeutic fluid is delivered 6. Electrical energy is provided by a power supply 240, located in the DP 200, and transmitted via wires and connectors 155 to at least two electrodes 16, 16' which generate a galvanic current in the subcutaneous tissue. In FIG. 25b the electrodes 16, 16' are disposed on a designated subcutaneously located element 67.

Figure 25C:
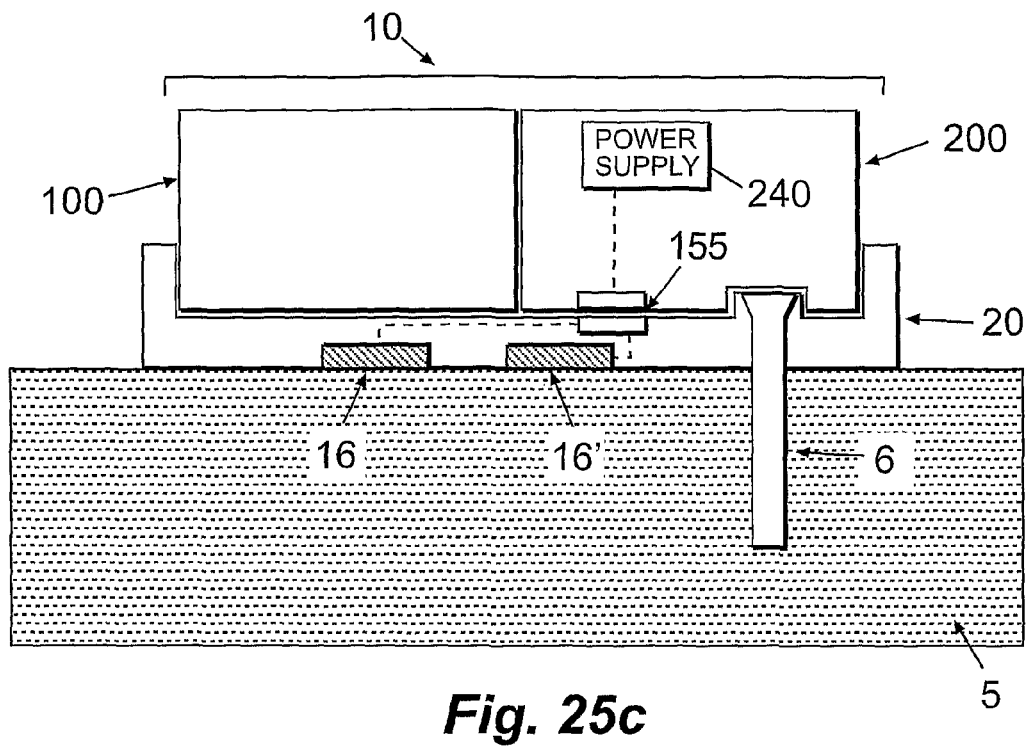

In FIG. 25c local vasodilation is achieved by transdermal current application. The electrodes 16 and 16' are located in the cradle unit 20. Connectors 155 located in the cradle unit 20 and in the DP 200 allow current supply from the power supply 240 in the DP 200 to the electrodes 16, 16' in the cradle unit 20 via wires.

Figure 25D:
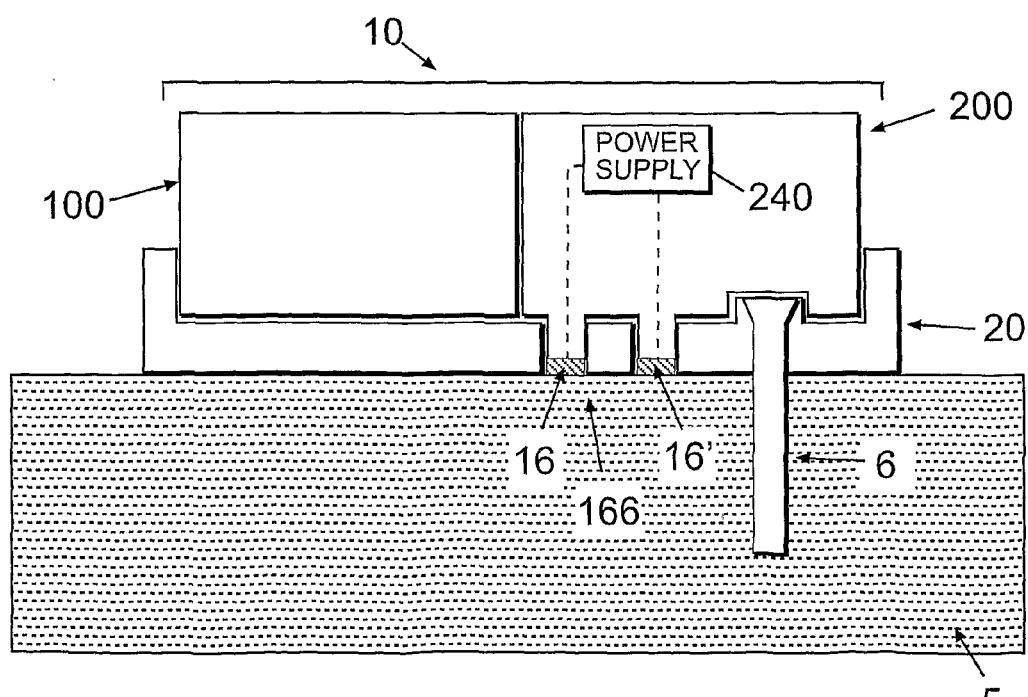

In FIG. 25d local vasodilation is achieved by transdermal current application wherein the electrodes 16, 16' are located in the RP 100 and openings 166 in the cradle unit 20 enable direct current transmission to the user's skin.

FIGS. 26a-d shows four different embodiments of a dispensing patch unit 10 comprising a component capable of enhancing subcutaneous insulin absorption by application of laser that emits light in the UV range. Application of the UV laser beam may be either continuous or pulsed. Use of a pulsed laser reduces heat built-up and subsequent damage to the tissue. According to one such embodiment, the UV light is in the range of 150-400 nm.

Figure 26A:
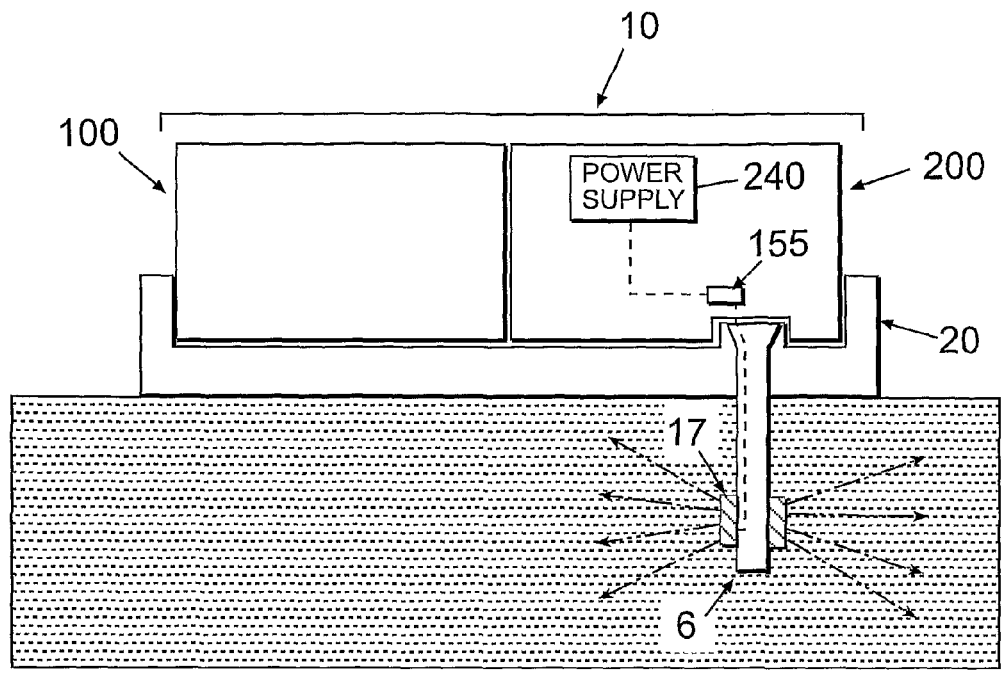
FIGS. 26a-26d show four different embodiments of a dispensing patch unit comprising means for enhancing subcutaneous insulin absorption by laser that emits light in the UV range.
Figure 26B:
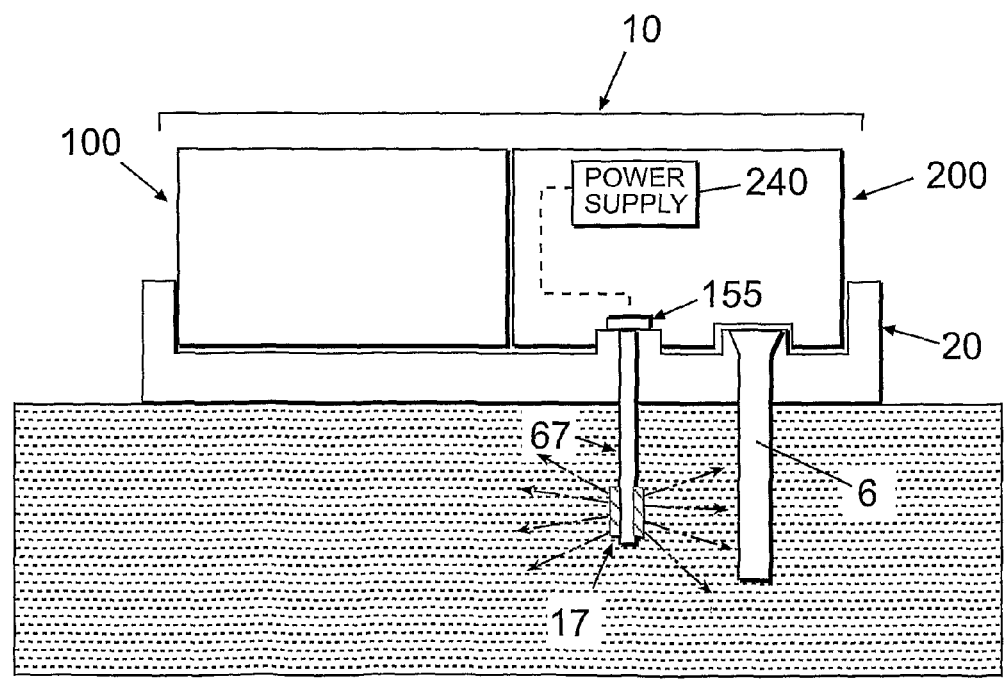

In FIG. 26a-26b local vasodilation is achieved by application of laser that emits light in the UV range, wherein the light source is on the surface of a subcutaneously inserted cannula or probe. Electrical energy is provided by a power supply 240, located in the DP 200, and transmitted via wires and connectors 155 to at least at least one light source 17 which emits light in the UV range in the subcutaneous tissue.

In FIG. 26a the light source 17 is located on the same cannula through which the therapeutic fluid is delivered 6.

In FIG. 26b the light source 17 is located on a designated subcutaneously located element 67.

Figure 26C:
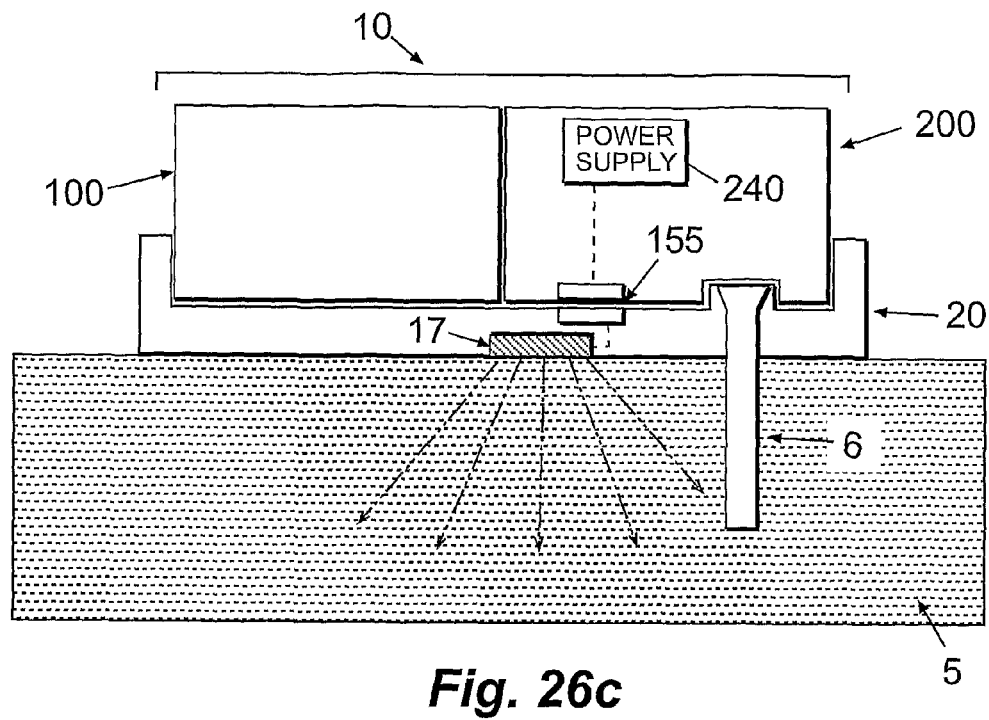

In FIG. 26c local vasodilation is achieved by transdermal UV light application. The light source 17 is located in the cradle unit 20. Connectors 155 located in the cradle unit 20 and in the DP 200 allow current supply from the power supply 240 in the DP 200 to the electrode 16 in the cradle unit 20 via wires.

Figure 26D:
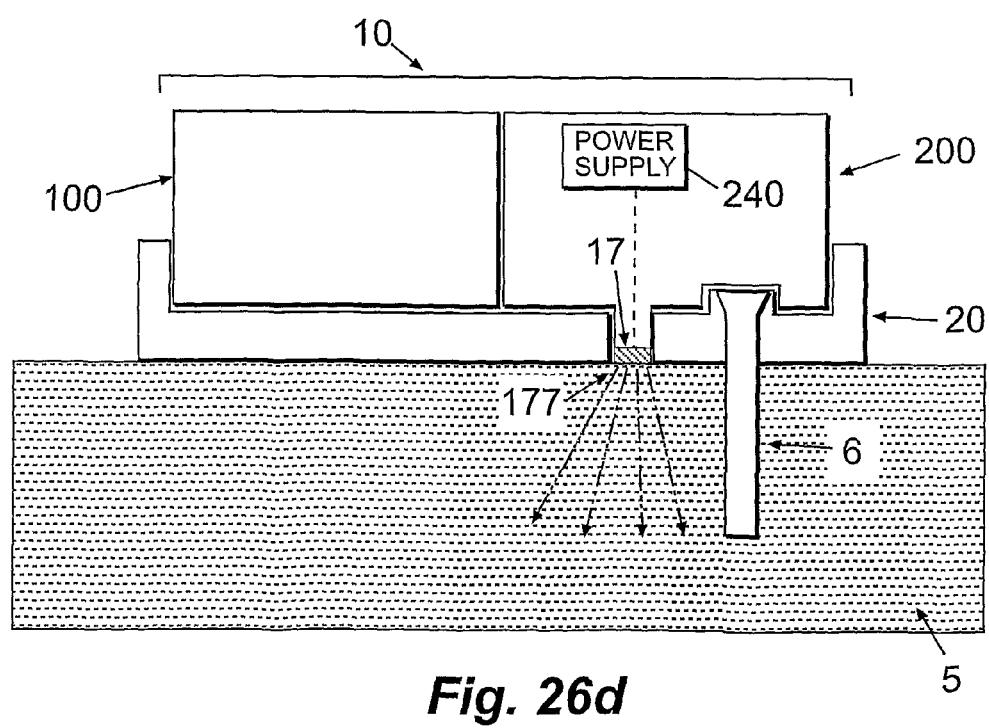

In FIG. 26d local vasodilation is achieved by transdermal UV light application wherein the light source 17 is located in the RP 100 and an opening 177 in the cradle unit 20 enables direct light transmission to the user's skin.

Figure 27:
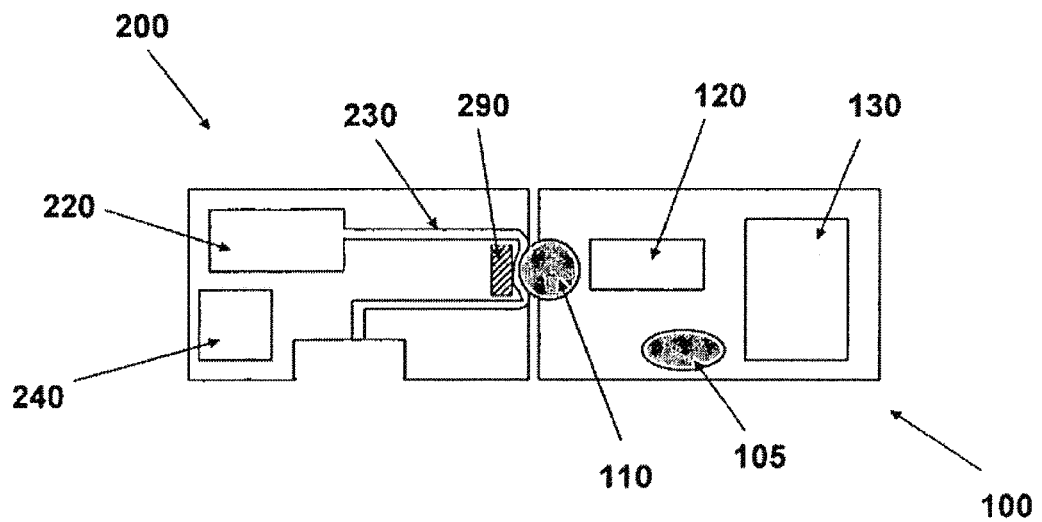
FIG. 27 is detailed schematic description of a two-part patch unit employing a peristaltic pumping mechanism.

FIG. 27 shows (via FIGS. 27A and 27B) a two-part patch unit 10 comprised of a reusable part 100 and a disposable part 200. Reusable part 100 may comprise manual buttons/switches 105, positive displacement pump provided with rotary wheel 110, driving mechanism 120 and/or electronic components 130. Disposable part 200 may include a reservoir 220, delivery tube 230, energy supply means 240 and/or stator 290. The disposable components are used until emptying of the reservoir 220. Rotation of the wheel and pressing of rollers against the stator 290 periodically positively displaces fluid within the delivery tube 230 by virtue of a peristaltic motion. An example of suitable positive displacement pump is disclosed in commonly owned application U.S. Ser. No. 11/397,115, which is hereby incorporated by reference. Driving mechanism 120 is provided (e.g. a stepper motor, a DC motor, a SMA actuator or the like), which rotates the rotary wheel and is controlled by electronic components residing in the reusable part 100 of the patch unit 10. Among such electronic components can be controller, processor and/or transceiver. The electronic components are schematically designated by a common numeral 130. An appropriate power supply 240 is also provided, which may include one or more batteries. Infusion programming can be carried out by a remote controller (not shown) having a bidirectional communication link with the transceiver provided in the patch unit 10. Alternatively or additionally, the infusion programming can be carried out by manual buttons/switches 105 provided on the patch unit 10.

Figure 28:
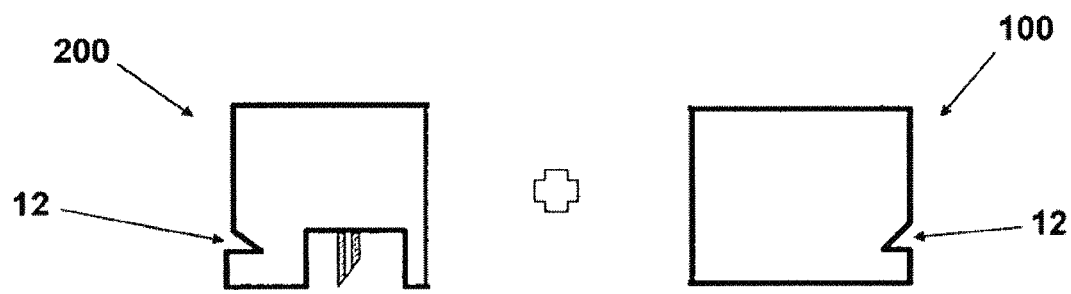
FIG. 28 is a schematic cross-sectional view of a two-part patch unit.
Figure 28:
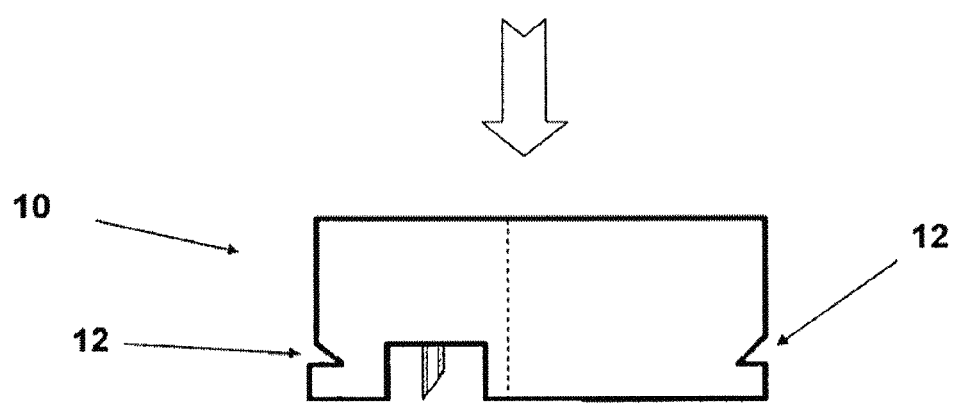

As depicted by FIG. 28, lateral notches 12 may be provided on exterior sides of both parts. Before connecting the patch unit 10 with the cradle unit 20 the disposable 200 and reusable 100 parts are attached to each other and constitute the single patch unit 10 as seen in FIG. 28.

Figure 29A:
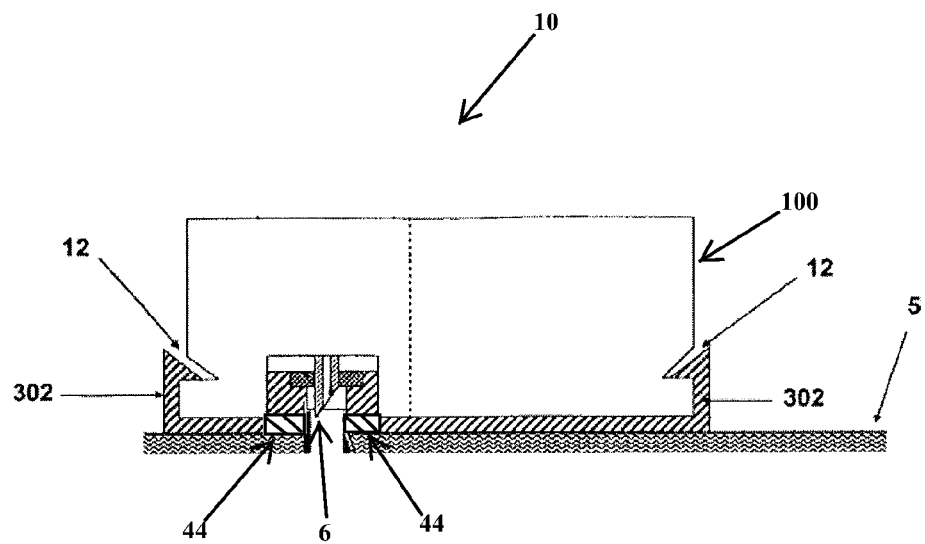
FIGS. 29A-29B are transverse cross-sectional views depicting connection of a patch unit to and disconnection of the patch unit from a cradle unit.
Figure 29B:
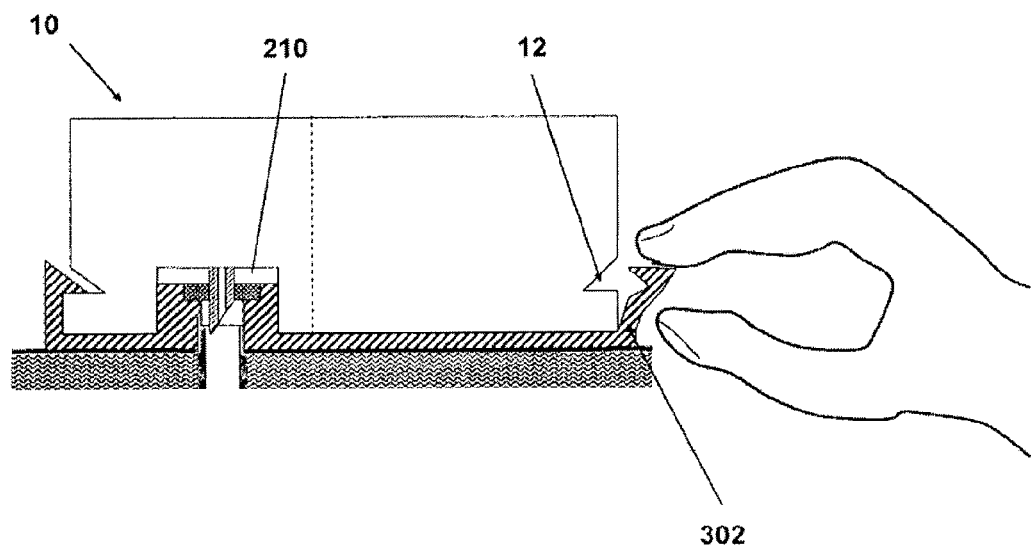

FIGS. 29A and 29B show an example of connection and disconnection of the patch unit 10 comprised of a reusable part 100 and a disposable part 200, and the skin-adherable cradle unit 20. FIG. 28 shows the two units before connection. When the patch unit 10 is brought into contact with the cradle unit 20 it is guided by the anchoring latches 302 maintaining precise alignment between the two units and anchoring of the two units. FIG. 29A shows the patch unit 10 after it has been connected to the unit 20 and secured due to snapping engagement of the anchoring latches 302 provided at the outside periphery of the unit 20 with the lateral notches 12 provided at the patch unit 10. FIG. 29B shows the patch unit 10 being disconnected by back-pulling the elastically deformable latches 302. Also illustrated are: the subcutaneously insertable element in the form of a cannula 6, an absorption enhancement device in the form of a heating plate 44, the well 210, and the user's skin 5.

Any and all references to publications or other documents, including but not limited to, patents, patent applications, articles, webpages, books, etc., presented in the present application, are herein incorporated by reference in their entirety.

Although a few variations have been described in detail above, other modifications are possible. For example, the logic flow depicted in the accompanying figures and described herein do not require the particular order shown, or sequential order, to achieve desirable results.

While the present invention has been described in terms of specific methods, structures, and devices it is understood that these are example embodiments only and that variations and modifications will occur to those skilled in the art upon consideration of the present invention. As well, the features illustrated or described in connection with one embodiment can be combined with the features of other embodiments. Such modifications and variations are intended to be included within the scope of the present invention. Those skilled in the art will appreciate, or be able to ascertain using no more than routine experimentation, further features and advantages of the invention based on the above-described embodiments. Accordingly, the invention is not to be limited by what has shown and particularly described, except as indicated by the appended claims particularly.

All publications and references are herein expressly incorporated by reference in their entirety. The terms "a" and "an" can be used interchangeably, and are equivalent to the phrase "one or more" as utilized in the present application. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

What is claimed is:

1. A system for delivering a therapeutic fluid to a body of a patient comprising:
    a pump including:
        a reservoir for retaining the therapeutic fluid,
        a driving mechanism which dispenses via pumping the therapeutic fluid from the reservoir to the body of the patient,
        electronic components which control, at least in part, operation of the driving mechanism, and
        a power supply which powers at least the driving mechanism and the electronic components;
    a first subcutaneously insertable element for delivering the therapeutic fluid therethrough to the body of the patient, the first subcutaneously insertable element comprises a distal portion configured for subcutaneous placement within the body of the patient; and
    an absorption enhancement device configured to contact and locally heat tissue of the patient surrounding the first subcutaneously insertable element when subcutaneously placed, which causes an increase in absorption rate of the therapeutic fluid in the body of the patient, wherein the electronic components control the operation of the absorption enhancement device, and wherein the electronic components are contained in a reusable part, and that the reservoir is contained in a disposable part, the disposable part also provides the first subcutaneously insertable element and the absorption enhancement device, and wherein the system further comprises a skin adherable cradle unit having an elastically deformable anchoring latch at each opposing end, such that one opposing end of the skin adherable cradle unit extends upward directly against and along an opposing exterior side of the reusable part, and an other opposing end of the skin adherable cradle unit extends upwardly directly against and along an opposing exterior side of the disposable part,
    the anchoring latches hold both the reusable part and the disposable part horizontally side-by-side via a snapping engagement of a top portion of the anchoring latches with a pair of lateral notches, where one lateral notch is provided on the opposing exterior sides of the reusable part and an other lateral notch is provided on the opposing exterior side of the disposable part,
    and wherein the first subcutaneously insertable element and the absorption enchancement device. extend downwardly in an opening provided in the skin adherable cradle unit such that the distal portion can be placed subcutaneously within the body of the patient, and the absorption enhancement device can contact and locally heat surrounding tissue of the patient when the first subcutaneously insertable element is subcutaneously placed.

2. The system of claim 1, wherein the absorption enhancement device comprises one or more heating plates disposed on the disposable part.

3. The system of claim 2, wherein the first subcutaneously insertable element is a cannula, the disposable part includes an outlet port from which the cannula extends, and wherein the one or more heating plates are arranged concentrically around the outlet port.

4. The system of claim 2, wherein the first subcutaneously insertable element is a cannula, the disposable part includes an outlet port from which the cannula extends, and wherein the one or more heating plates is a rounded heating plate arranged concentrically around the outlet port.

5. The system of claim 1, wherein the first subcutaneously insertable element is a cannula, and wherein the absorption enhancement device comprises at least one electrode associated with the cannula.

6. The system of claims 1, wherein the absorption enhancement device is electrically connected to the power supply.

7. The system of claim 1, wherein the absorption enhancement device is activated in accordance with a planned meal.

8. The system of claim 1, wherein the therapeutic fluid comprises insulin.

9. The system of claim 1, wherein the electronic components control the operation of the absorption enhancement device, wherein the first subcutaneously insertable element is a cannula, wherein the disposable part includes an outlet port from which the cannula extends, the absorption enhancement device comprises one or more heating plates disposed on the disposable part and arranged concentrically around the outlet port, and wherein the absorption enhancement device is electrically connected to the power supply.

10. The system of claim 1, wherein the power supply is provided in the disposable part.

11. The system of claim 1, wherein the power supply is provided in the reusable part.

\* \* \* \* \*